(12) United States Patent
Drasler et al.

(10) Patent No.: US 11,571,295 B2
(45) Date of Patent: *Feb. 7, 2023

(54) MITRAL VALVE WITH FREE EDGE SUPPORT

(71) Applicants: William Joseph Drasler, Minnetonka, MN (US); William Joseph Drasler, II, Minnetonka, MN (US)

(72) Inventors: William Joseph Drasler, Minnetonka, MN (US); William Joseph Drasler, II, Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/547,788

(22) Filed: Aug. 22, 2019

(65) Prior Publication Data

US 2019/0388222 A1 Dec. 26, 2019

Related U.S. Application Data

(63) Continuation of application No. 15/622,168, filed on Jun. 14, 2017, now Pat. No. 10,463,482.

(51) Int. Cl.
*A61F 2/24* (2006.01)

(52) U.S. Cl.
CPC .......... *A61F 2/2418* (2013.01); *A61F 2/2454* (2013.01); *A61F 2210/0014* (2013.01); *A61F 2220/005* (2013.01); *A61F 2220/0016* (2013.01); *A61F 2220/0058* (2013.01); *A61F 2220/0075* (2013.01); *A61F 2220/0083* (2013.01); *A61F 2230/0006* (2013.01); *A61F 2230/0008* (2013.01); *A61F 2230/0067* (2013.01); *A61F 2230/0069* (2013.01); *A61F 2230/0095* (2013.01); *A61F 2250/0003* (2013.01); *A61F 2250/0069* (2013.01)

(58) Field of Classification Search
CPC .................. A61F 2/2418; A61F 2/2454; A61F 2210/0014; A61F 2220/0016; A61F 2220/005; A61F 2220/058; A61F 2220/0075; A61F 2220/0083; A61F 2230/0006; A61F 2230/0008; A61F 2230/0067; A61F 2230/0069; A61F 2230/0095; A61F 2250/0003; A61F 2250/0069; A61F 2220/0058

See application file for complete search history.

(56) References Cited

U.S. PATENT DOCUMENTS

| 6,332,893 B1 * | 12/2001 | Mortier | A61F 2/2487 623/2.41 |
| 6,797,002 B2 * | 9/2004 | Spence | A61F 2/2457 623/2.38 |
| 10,172,710 B2 * | 1/2019 | Drasler | A61F 2/2433 |
| 10,463,482 B2 * | 11/2019 | Drasler | A61F 2/2454 |

(Continued)

*Primary Examiner* — Paul B Prebilic

(57) ABSTRACT

A transcatheter stent-valve having replacement leaflets that are attached along their free edges. The stent-valve frame has supports that extend distally of the replacement leaflets to two fastening sites. The replacement leaflets are attached along a leaflet base forming a linear attachment to the stent-valve frame. The free edges of the leaflets have cords attached; the cords attach the free edges of the leaflets to the fastening sites located on the supports. The stent-valve can be a single component stent-valve or it can be a second component of a dual component stent-valve.

13 Claims, 25 Drawing Sheets

(56) References Cited

U.S. PATENT DOCUMENTS

| | | | | |
|---|---|---|---|---|
| 2005/0075727 A1* | 4/2005 | Wheatley | .............. | A61F 2/2457 |
| | | | | 623/902 |
| 2006/0149368 A1* | 7/2006 | Spence | ................ | A61F 2/2445 |
| | | | | 623/2.37 |
| 2007/0282429 A1* | 12/2007 | Hauser | .................. | A61F 2/2445 |
| | | | | 623/1.36 |
| 2008/0300678 A1* | 12/2008 | Eidenschink | ......... | A61F 2/2418 |
| | | | | 623/2.18 |
| 2020/0405480 A1* | 12/2020 | Rowe | ................... | A61F 2/2418 |

* cited by examiner

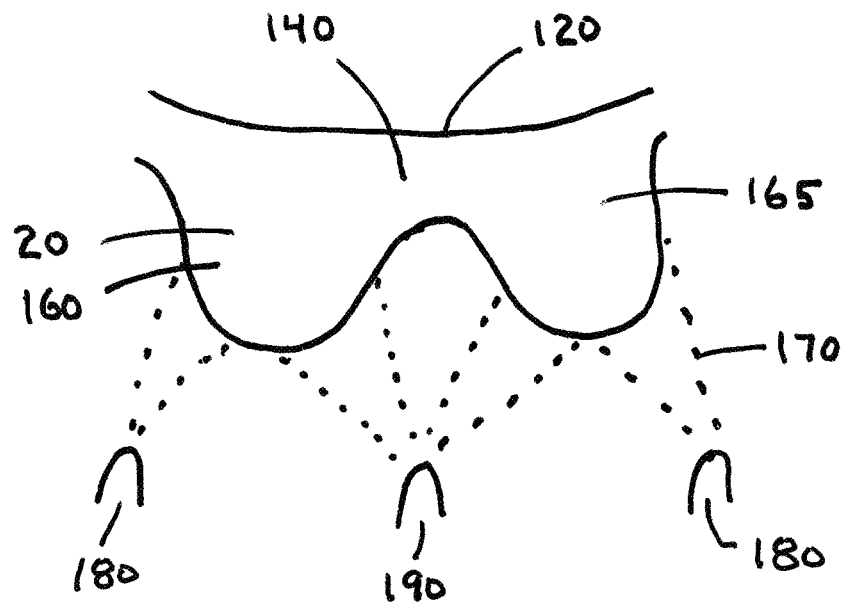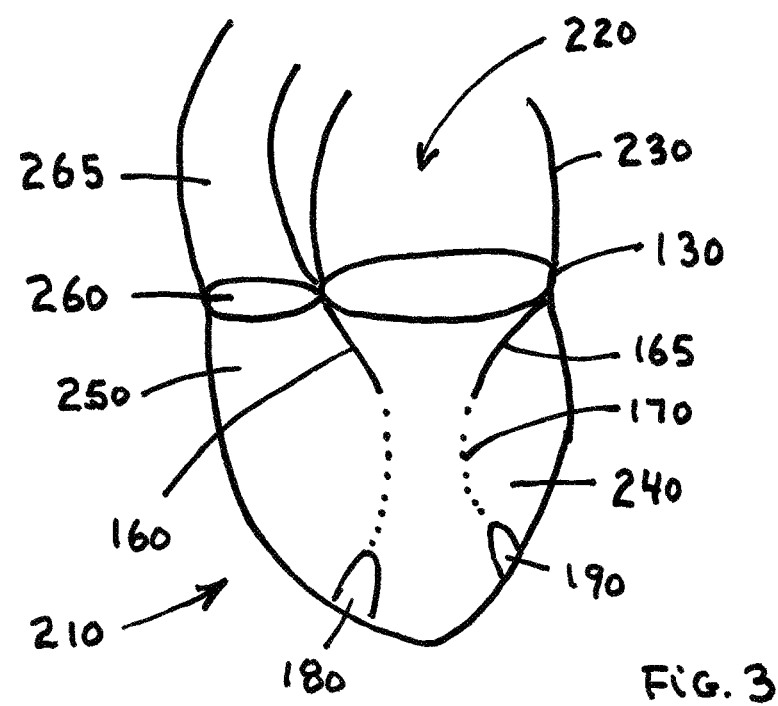

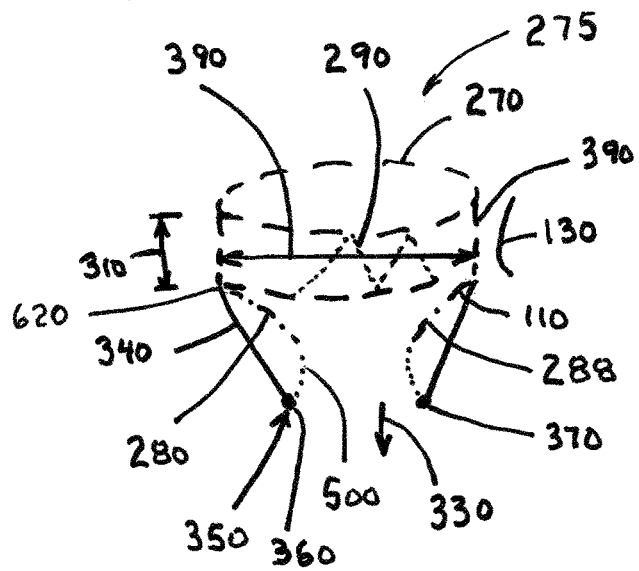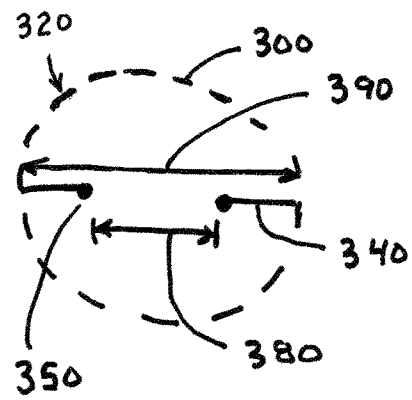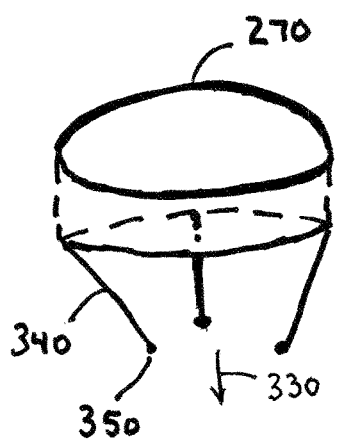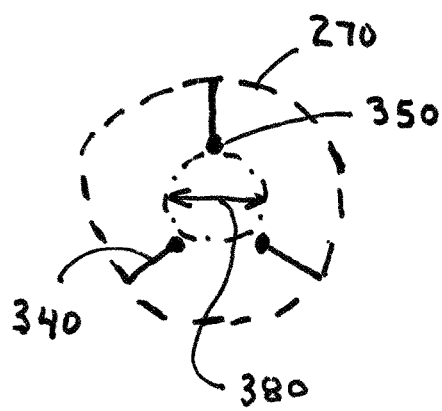

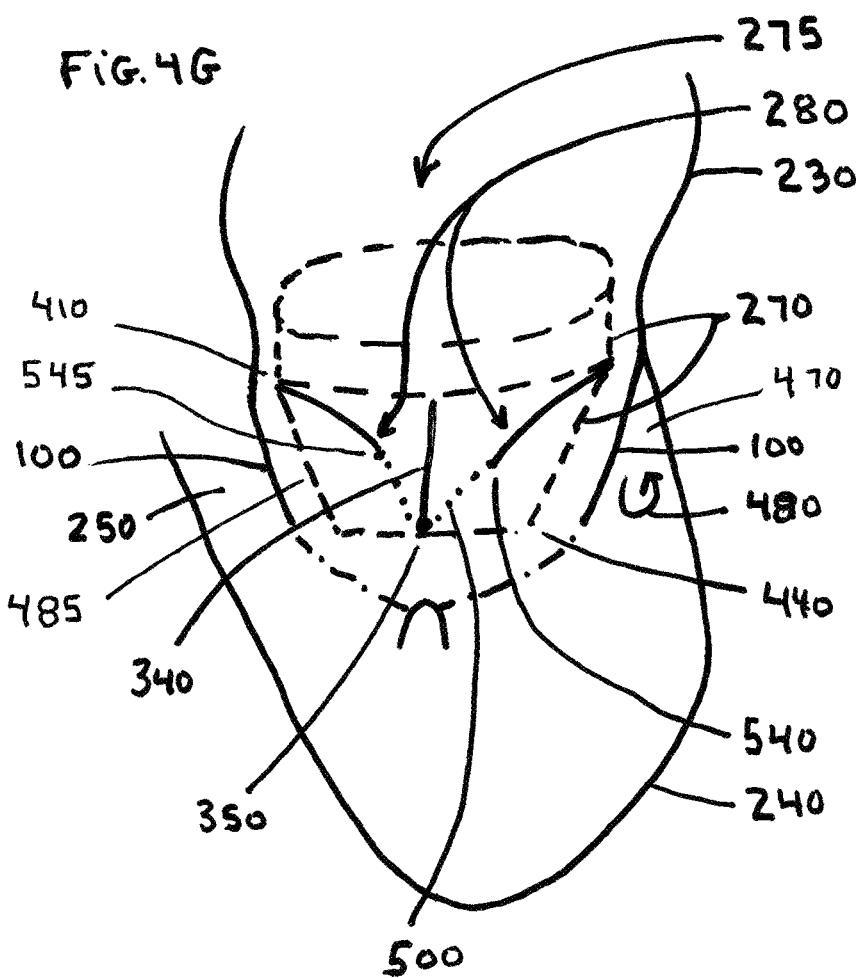

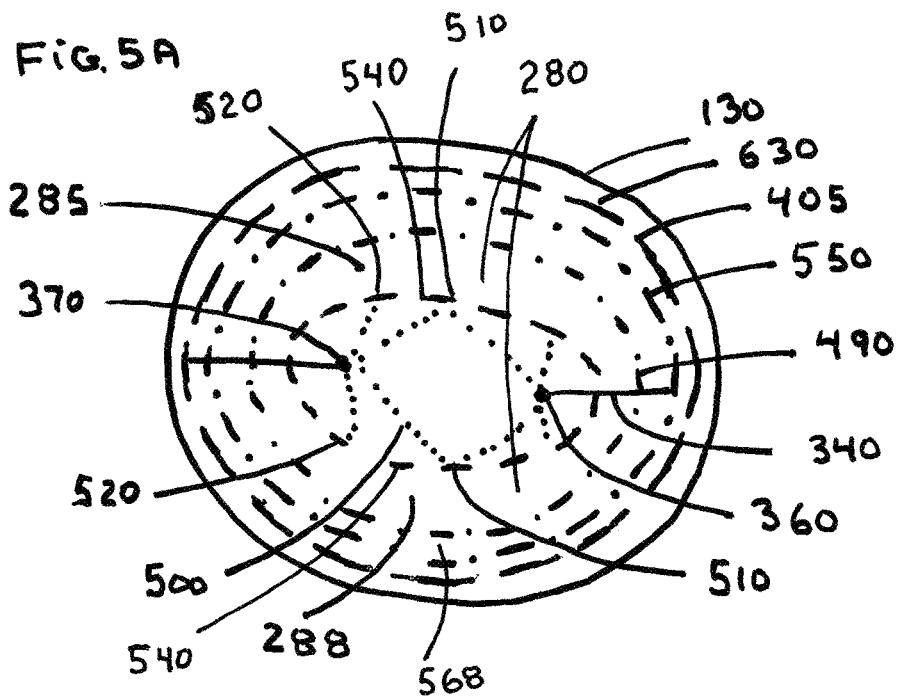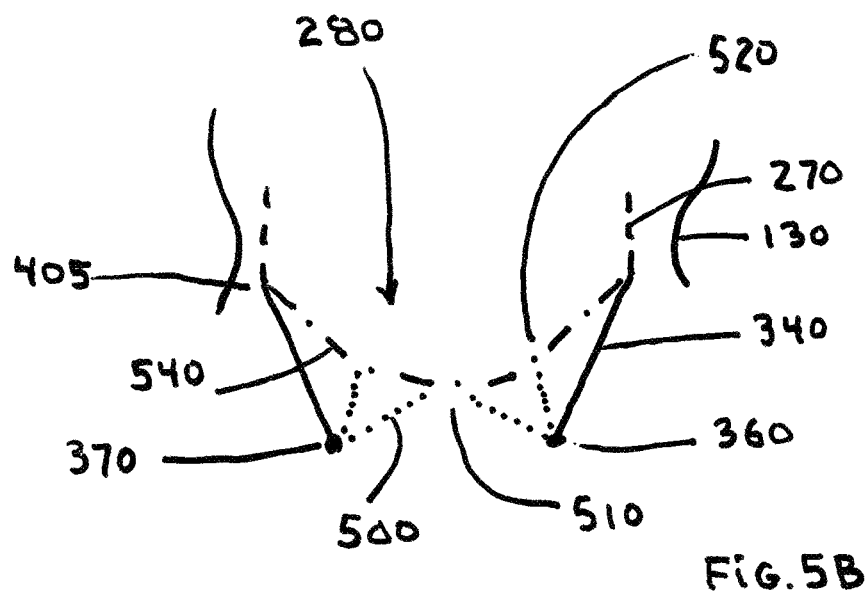

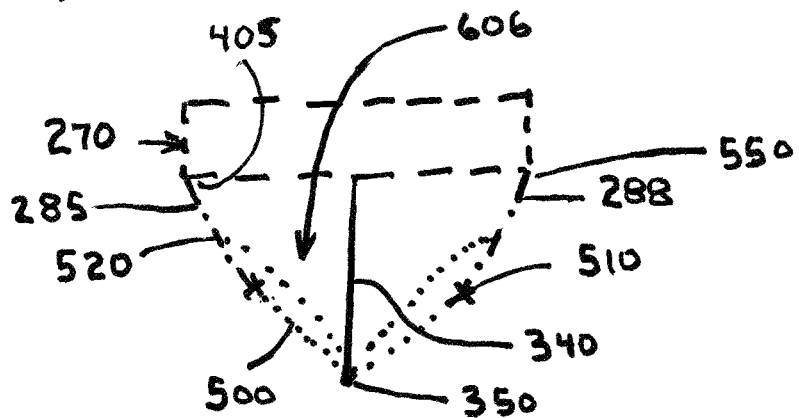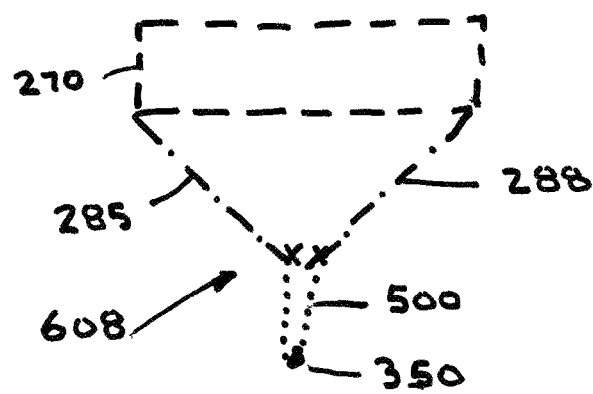

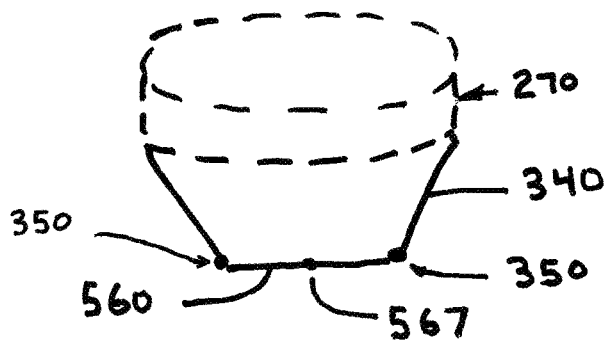
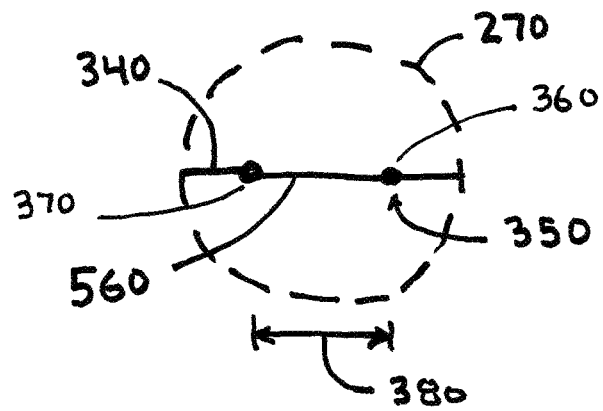
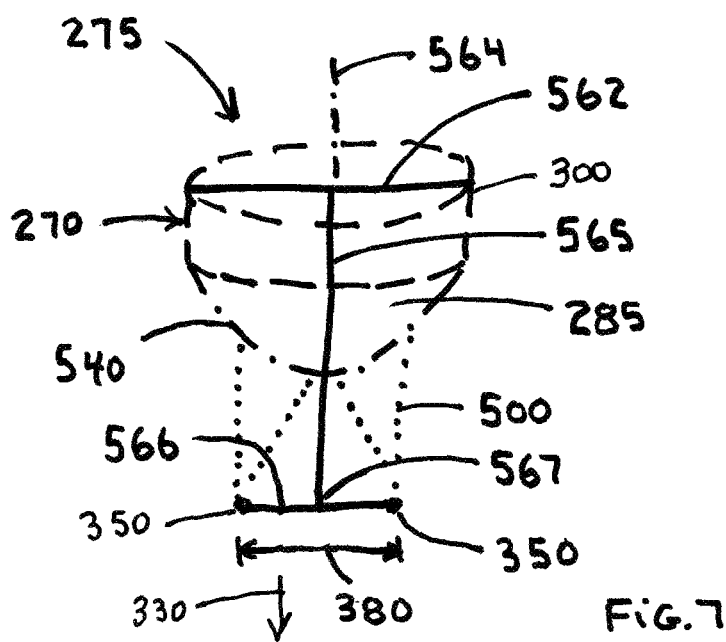

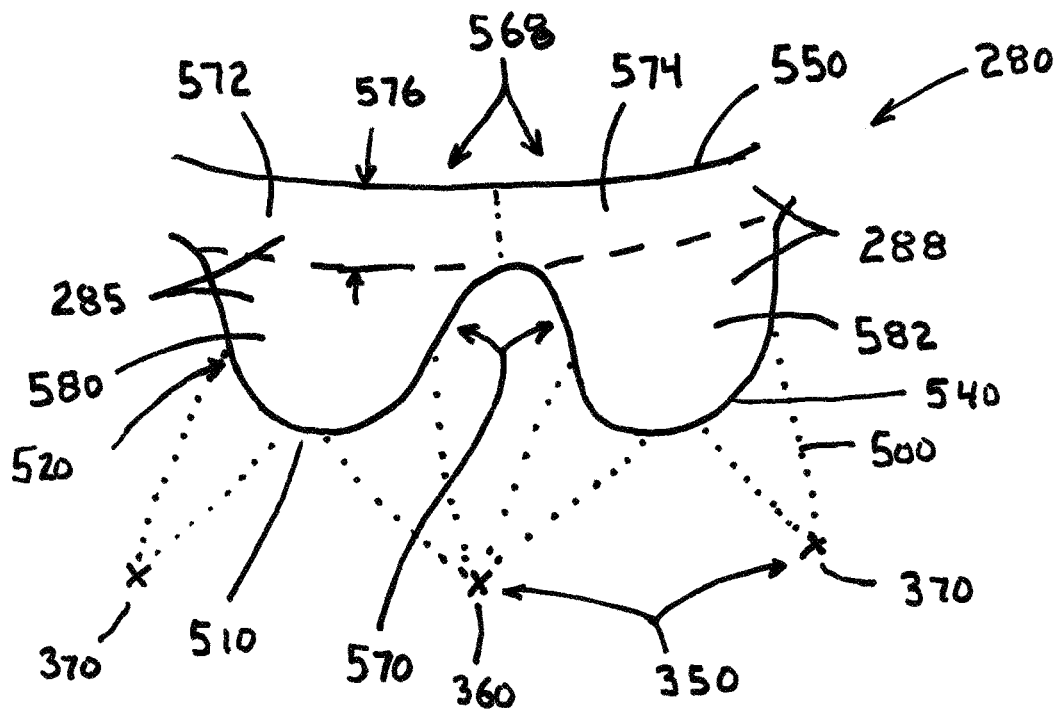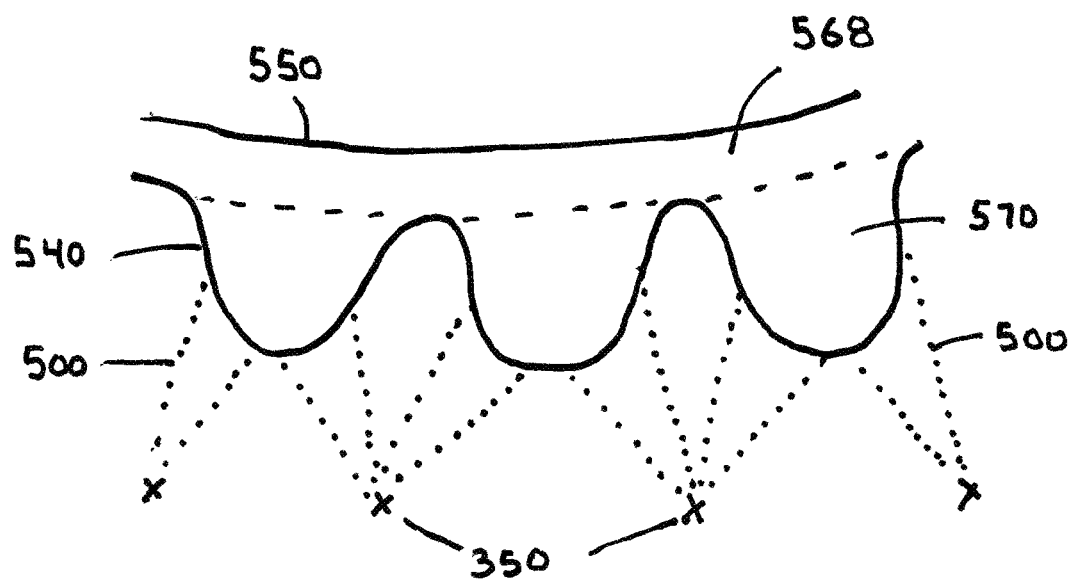

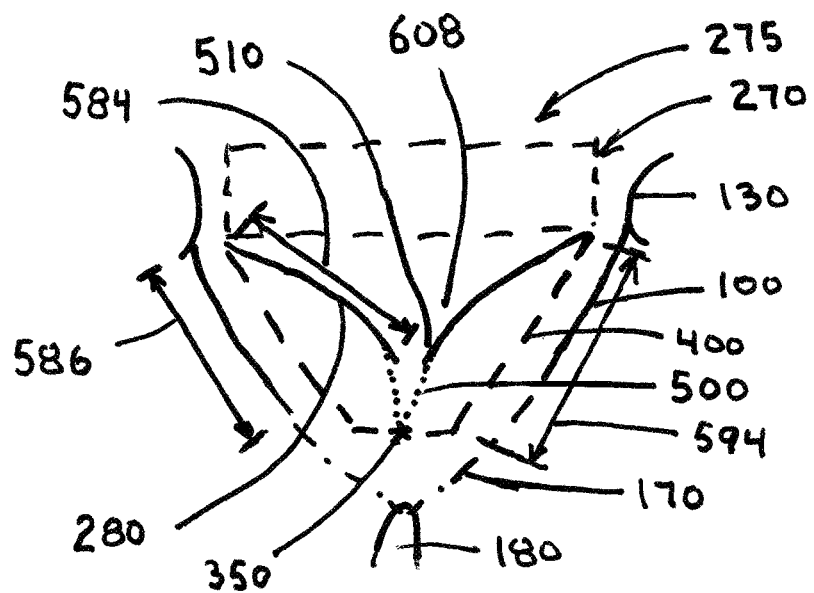
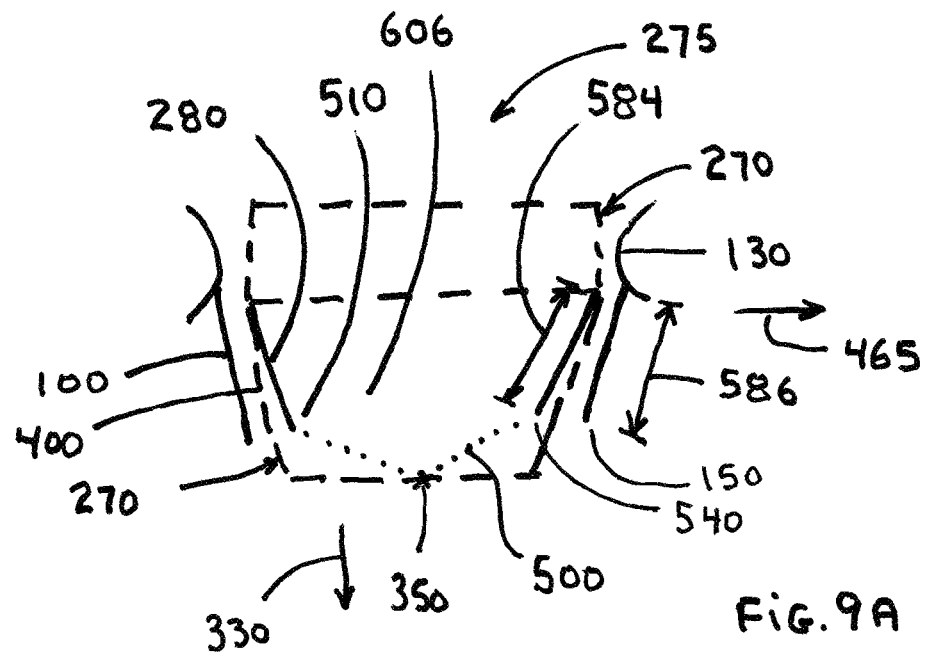

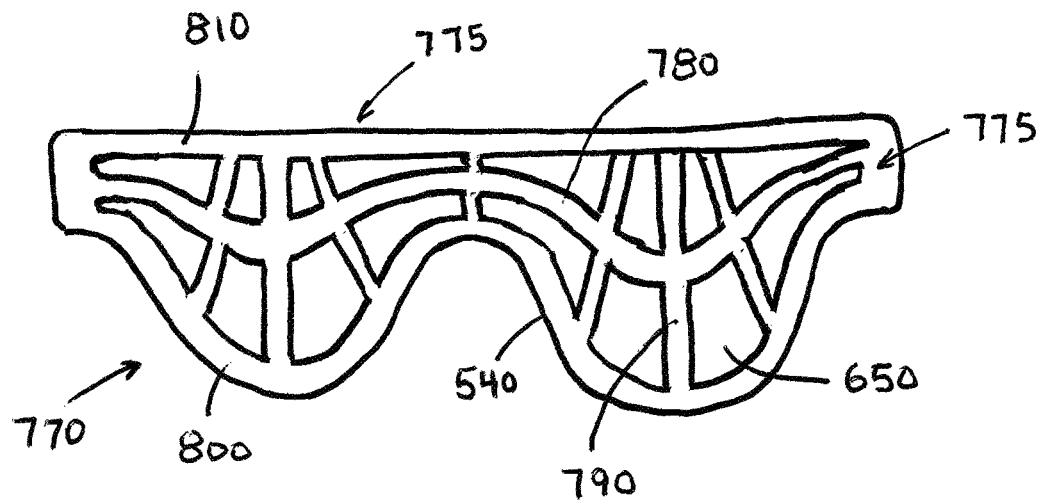
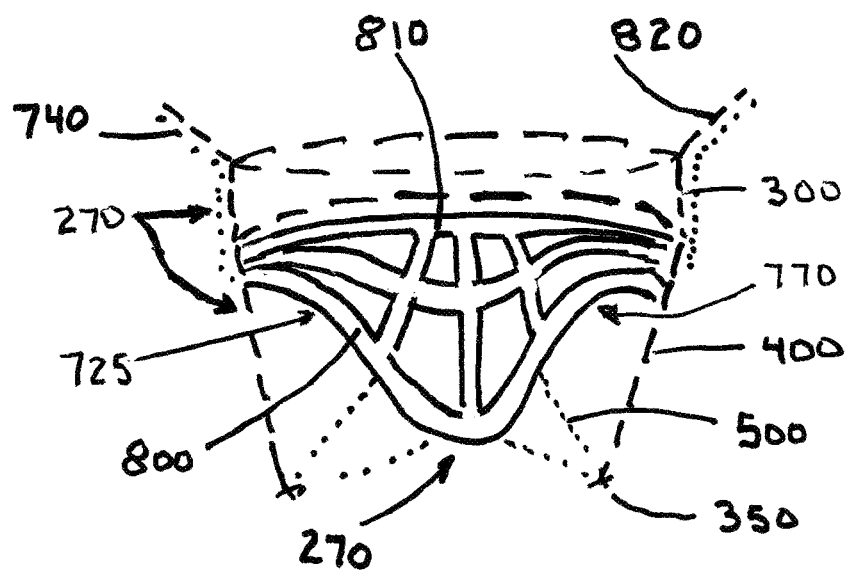

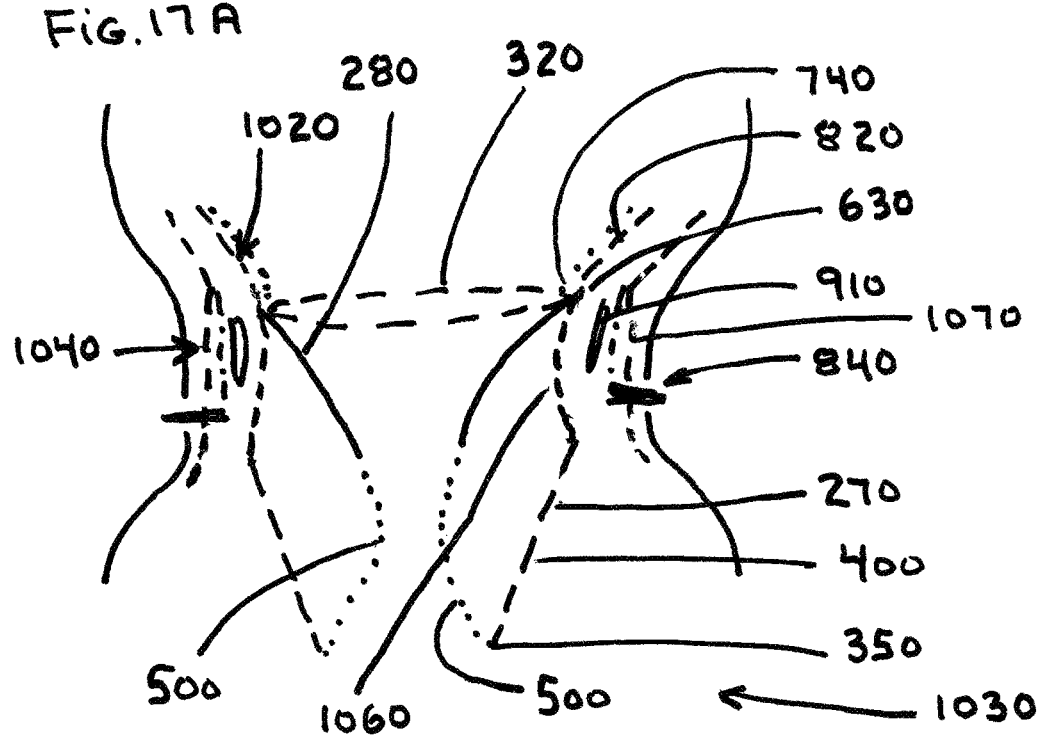
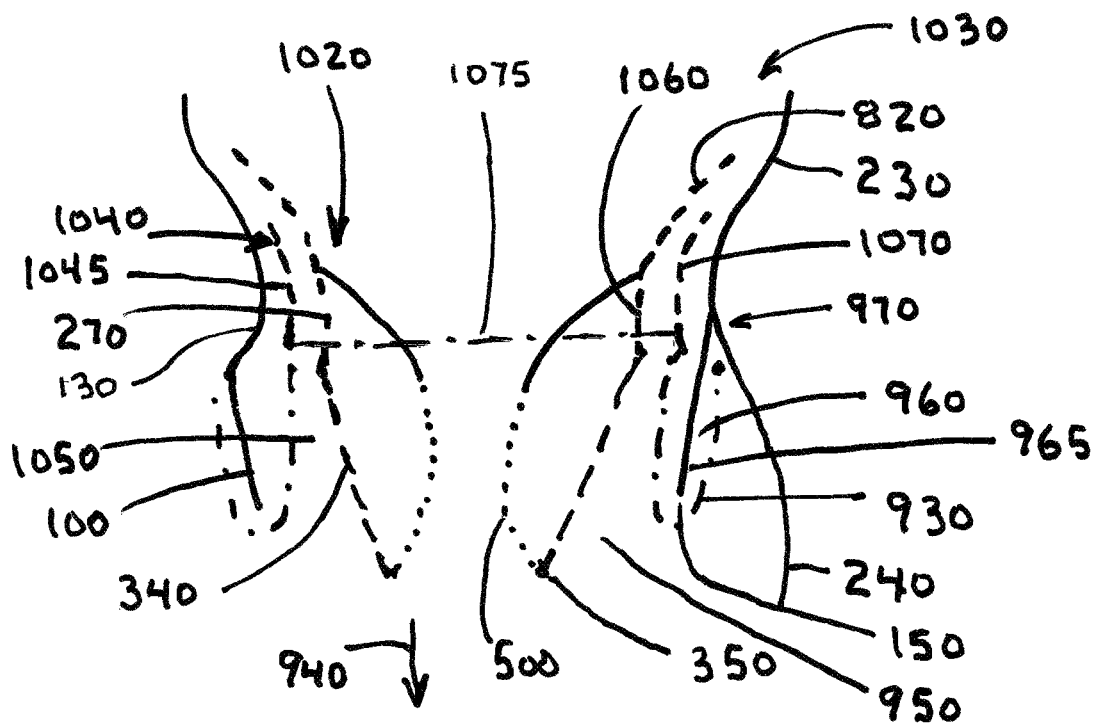

MITRAL VALVE WITH FREE EDGE SUPPORT

CROSS REFERENCE TO RELATED APPLICATIONS

This patent application is a continuation of application Ser. No. 15/622,168 filed 14 Jun. 2017, now issued U.S. Pat. No. 10,463,482 with the title Free Edge Supported Mitral Valve and naming William J. Drasler and William J. Drasler II as inventors, the entire content of which is hereby incorporated herein by reference in its entirety. This patent application makes reference to and thereby incorporates all information found in nonprovisional patent application Ser. No. 15/457,626 entitled Two Component Mitral Valve filed 13 Mar. 2017, now U.S. Pat. No. 10,172,710, by William J. Drasler, et. al.

BACKGROUND OF THE INVENTION

Transcatheter mitral valve replacement (TMVR) devices are currently being designed and tested clinically to provide therapy to patients suffering from mitral regurgitation. One potential problem that presently is faced by current TMVR devices is their profile and stiffness; another problem is associated with the axial length of the stent frame which can impinge upon the native anterior mitral leaflet and cause blockage of the left ventricular outflow tract (LVOT). The longer axial length of the current stent frames is needed to support the attachment of the standard TMVR semi-lunar shaped replacement leaflets and provide the necessary strength and lever arm needed to ensure that the replacement leaflets do not evert during systole. Much of the profile for the TMVR devices is related to the thickness of the leaflets; the leaflet thickness is needed to provide the strength needed to support the stresses imposed by the blood pressure onto the replacement leaflets during systole. Further, the current TMVR devices often create stagnation zones that lead to thrombus formation that result in the formation and release of harmful thromboemboli. What is needed is a low profile TMVR device that does not impinge upon the native anterior mitral valve leaflet and does not have a tendency to generate potentially harmful thromboemboli.

SUMMARY

The present invention is a transcatheter heart valve with leaflets that are supported along their free-edge in a manner that is similar in design to the native mitral valve or the native tricuspid valve found in the heart. The present invention can be applied to any of the four valves of the heart although the present specification will focus on its application to TMVR.

The current transcatheter aortic valve replacement (TAVR) devices have been directed toward the semi-lunar valve leaflet designs similar to native aortic valves of the heart and similar to those used in surgical tissue heart valves; such replacement devices have been successfully utilized in the clinic. The attachment of the semi-lunar leaflets to the cylindrical wall of the stent frame follows a crown-shaped pattern that requires an axial distance for the attachment in order to provide the strength and torque lever arm to the leaflet necessary to prevent leaflet eversion; the free edges of the semi-lunar leaflets are not attached to the wall of the stent except at points which is referred to as commissures; where the free edge attaches the leaflet to the cylindrical vessel wall; the free edges of the semi-lunar leaflets coapt with each other at the downstream end of the valve to prevent retrograde blood flow. The present invention provides a different shape for the leaflets, one that attaches the entire free edge of the leaflet to a series of cords; the cords are attached to fastening sites that are fixed in space at a location that is downstream of the replacement valve leaflets. The fastening sites serve a similar function to the papillary muscles found in the human heart; the cords serve a similar function to the cordae tendineae of the heart. The free edges of the present invention also coapt with each other at the downstream end of the valve to prevent retrograde flow of blood.

The attachment of the leaflet base of the present invention to the stent frame follow a linear attachment around a circular or oval shape rather than a crown-shaped attachment. The linear attachment does not require an axial length component to provide torque strength to the valve leaflets to prevent eversion; instead the cords provide the strength to prevent leaflet eversion. The linear attachment allows the length of the stent frame, which supports the replacement leaflets (in the present embodiment the linear attachment is located adjacent to the mitral annulus) to be shorter than a stent frame that supports a semi-lunar shaped leaflet; the short frame length of the present invention provides an advantage for not causing impingement onto the anterior mitral valve leaflet; such impingement can result in resistance to blood flow in the LVOT. The attachment of the cords to the free edge of the present leaflets allows the leaflets to be thinner than leaflets used in semi-lunar valves thereby allowing the profile (i.e., delivery diameter for the device) for the TMVR device to be smaller and more easily delivered to the proper location across the mitral valve of the heart. Blood flow across the present stent-valve eliminates all regions for potential blood flow stagnation that can result in the formation of thrombus.

In one embodiment two supports are extended from each side of the stent frame downstream and into the left ventricle (LV); the supports can extend in a direction that is both downstream and also extending such that the supports end at fastening sites that have a smaller distance from each other than the diameter of the stent frame that is located in the mitral valve annulus. The free-edge supported leaflets of the present invention are attached at their free edges via cords to the fastening sites. A stent-like structure that forms an expandable frustum (smaller diameter end of frustum is located downstream of the larger diameter end) is attached to the downstream end of the stent frame. The supports are either attached to the expandable frustum, or the stent-like structure of the expandable frustum becomes the supports and the fastening sites are located at the downstream end of the expandable frustum.

In an alternate embodiment, three or more supports are attached along the perimeter of the stent frame and extend downstream into the LV. The plurality of supports can be used to support three or more cusps of the free-edge supported leaflets of the present invention which are attached via cords to the plurality of fastening sites.

In still another embodiment the fastening sites can be attached to each other by a lower support arm which supplies strength and stability to the fastening site.

In yet another embodiment two or more supports located along the perimeter of the stent frame extend downstream of the stent frame into the LV but meet at a single fastening point that is located downstream of the free-edge supported leaflets. The free edges of the plurality of leaflets are attached to one or more fastening sites via a plurality of cords.

In still yet another embodiment a single support is attached to the stent frame and extends downstream along a centerline axis of the mitral valve and stent frame ending in one or more fastening site that are located downstream of the replacement leaflets. The free edge of two or more free-edge supported leaflets are attached via a plurality of cords to the one or more fastening sites.

BRIEF DESCRIPTION OF THE DRAWING

FIG. 2C is a plan view of bicuspid heart valve leaflets splayed out onto a flat surface and attached to two papillary muscles.

FIG. 3 is a perspective view of the heart showing the native anterior and posterior valve leaflets attached to the mitral annulus.

FIG. 4A is a perspective view of a stent-valve frame having a waist and having supports attached to the waist and extending downstream to fastening sites located at the distal end of the supports.

FIG. 4B is a top view of the stent-valve frame showing the supports extending inwards to a fastening site distance that is smaller than the waist diameter.

FIG. 4C is a perspective view of the stent-valve frame having three supports that are attached to the waist.

FIG. 4D is a top view of the stent-valve frame having three supports attached to the waist.

FIG. 4G is a plan view of the stent-valve frame of FIG. 4F from a direction perpendicular to FIG. 4F.

FIG. 5A is a top view of the native mitral valve annulus having a stent-valve frame positioned adjacent the annulus; the stent-valve frame is attached to the replacement leaflets via a linear attachment and the free edges of the leaflets are attached to the fastening sites via cords.

FIG. 5B is a plan view of the stent-valve frame showing the anterior replacement leaflet attached at its free edge via cords to both the lateral fastening site and the medial fastening site.

FIG. 5C is a plan view of the stent-valve frame showing the anterior and posterior replacement leaflets attached at their free edges via cords to one of the fastening sites during diastole with the leaflets in an open configuration.

FIG. 5D is a plan view of the stent-valve frame showing the anterior and posterior replacement leaflets attached at their free edges via cords to one of the fastening sites during systole with the leaflets in an closed configuration.

FIG. 5E is a perspective view of an anterior replacement leaflet that is attached to both the medial fastening site and the lateral fastening site.

FIG. 6A is a perspective view of a stent-valve frame having supports connected at their distal ends via a lateral support arm.

FIG. 6B is a top view of the stent-valve frame of FIG. 6A having supports connected at their distal ends via a lateral support arm.

FIG. 7 is a perspective view of a stent-valve frame showing an anterior replacement leaflet attached via its free edge to a lower support arm.

FIG. 8C is a plan view of replacement leaflets splayed out flat showing two leaflet cusps attached via the free edge to medial and lateral fastening sites.

FIG. 8D is a plan view of replacement leaflets splayed out flat showing three leaflet cusps attached via the free edge to three separate fastening sites.

FIG. 9A is a plan side view of the stent-valve frame with the free edges of the replacement leaflets attached to fastening sites via cords; the replacement leaflets are in an open configuration allowing blood to flow from the LA to the LV.

FIG. 9B is a plan side view of the stent-valve frame with the replacement leaflets in a closed configuration; the replacement leaflets are longer than the native leaflets to ensure that the replacement leaflets will have an exposed area that blood pressure will act upon to close the leaflets during systole.

FIG. 15A is a plan view of leaflet frame that is formed from a thin metal or polymeric film; the leaflet frame is embedded within or sandwiched between polymeric or tissue matrix material to provides strength to the replacement leaflets and provide durable attachments sites for the replacement leaflets.

FIG. 15B is a plan view of a stent-valve frame having replacement leaflets as described in FIG. 15A attached to the stent frame and attached via cords to fastening sites.

FIG. 17A is a plan view of a dual component stent-valve having a first component that is attached to the native annulus via barbs that are activated from inflation of a torus balloon; a second component is placed in the open central lumen of the first component; the second component has free-edge supported replacement leaflets; the second component locks with the first component.

FIG. 17B is a plan view of a dual component stent-valve having a first component that is attached to the native valve leaflet via holding arms that extend around the native valve leaflets; a second component is placed in the open central lumen of the first component; the second component has free-edge supported replacement leaflets; the second component locks with the first component.

DETAILED DESCRIPTION

Figure 1A:
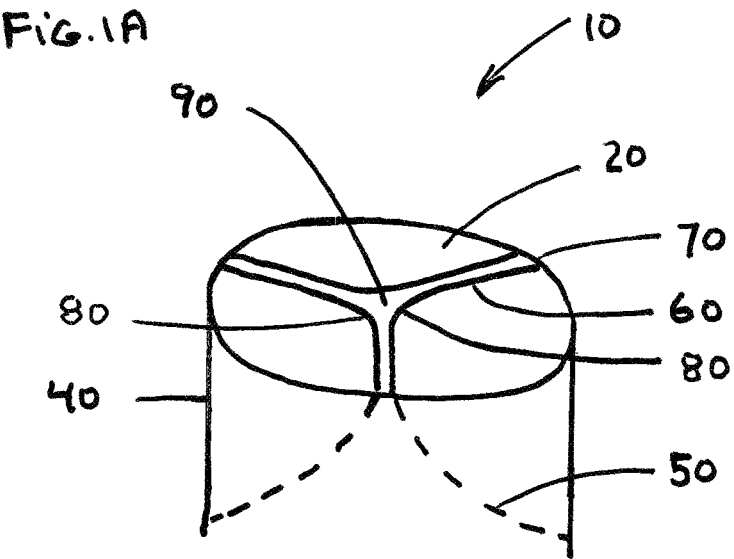
FIG. 1A is a perspective view of a native semilunar valve of the heart having unsupported free edges.
Figure 1B:
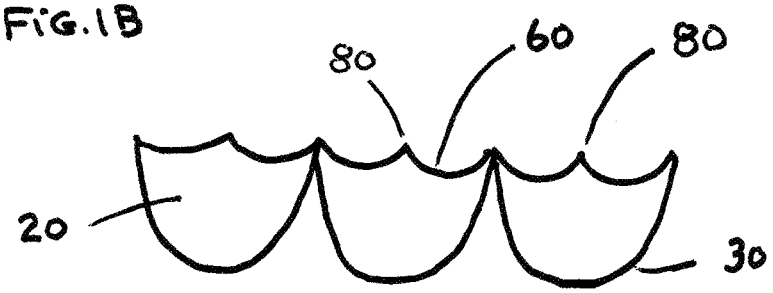
FIG. 1B is a plan view of native semilunar leaflets splayed out on a flat surface.

FIGS. 1A and 1B show a native semi-lunar valve (10) that is similar to the native valves found in the aortic and pulmonary positions within the heart and also found in most surgical tissue valves and in most TAVR devices. The leaflet cusps (20) or leaflets are attached at the leaflet crown-shaped attached edge (30) to the wall of the tubular structure wall (40) in a crown-shaped attachment (50). The unsupported free edges (60) of the leaflets are not attached to the wall of the support structure except at the location of the commissures (70) and the unsupported free edges (60) do not have any cordae tendineae or cords attached to them. The central free edge (80) of one leaflet forms a central junction (90) with the central free edge of another leaflet without any attachment to the support structure at the central junction.

Figure 2A:
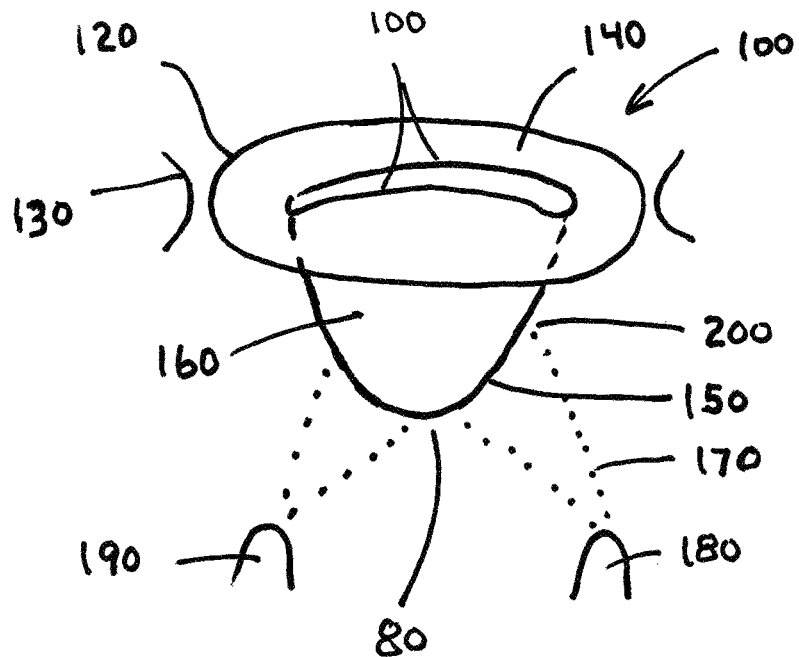
FIG. 2A is a perspective view of a native bileaflet heart valve showing the anterior leaflet attached to two separate papillary muscles.
Figure 2B:
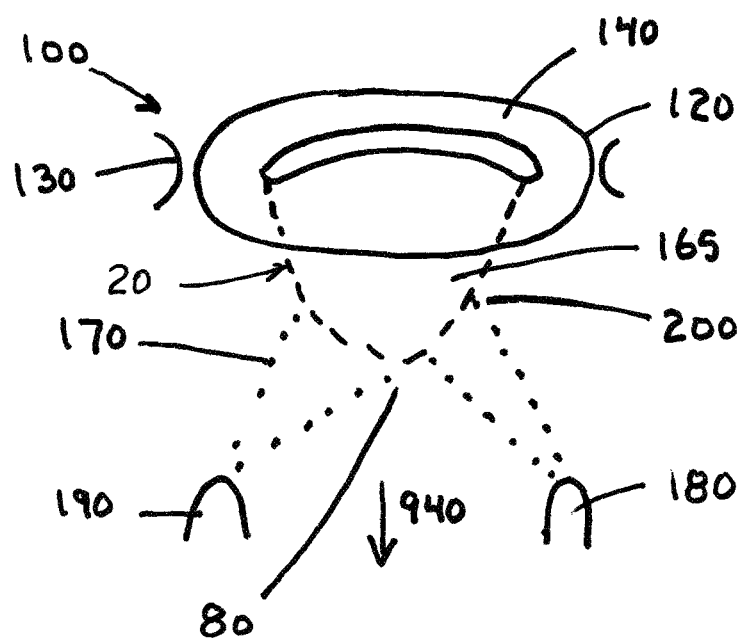
FIG. 2B is a perspective view of a native bileaflet heart valve showing the posterior leaflet attached to two separate papillary muscles.

FIGS. 2A-2C show native mitral valve leaflets (100) that have a linear attachment (120) to the mitral annulus (130) along a linear shape that forms a circle, oval path, or saddle-shaped path; the linear attachment is not a crown-shaped attachment path as found in semi-lunar valves such as native aortic valves; such semi-lunar valves have a crown-shaped attachment with axial componency that supports the leaflet from everting. A rim (140) of leaflet tissue extends from 2-6 mm along the perimeter of the mitral valve annulus (130) and extends toward the leaflets and forms two or more native leaflets (100) with native leaflet cusps (20) (i.e., 3 cusps for the tricuspid valve). As shown in FIG. 2A the supported free edge (150) of the anterior leaflet (160) is attached via cordae tendineae (170) to the anterior (or lateral) papillary muscle (180) and posterior (or medial) papillary muscle (190). The supported free edge (i.e., supported by and attached to the cordae tendineae (170)) moves into contact with the supported free edge of another mitral valve leaflet during systole to prevent blood flow from passing from the LV (240) to the LA (230) (shown in FIG. 3); the supported free edge of one leaflet moves away from another leaflet during diastole to allow blood to flow distally (940) through the valve. More than one cordae can attach from a papillary muscle to the anterior leaflet, for example; individual cordae can attach to an intermediate free edge (200), a central free edge (80), or other attachment sites along the free edge of a particular leaflet. FIG. 2B shows the posterior mitral leaflet (165) and the free edge attached to the posterior and anterior papillary muscles. The rim of the anterior and posterior leaflets is attached to the mitral annulus (130) along a linear circular, oval, or saddle-shaped path that is not crown-shaped.

FIG. 3 shows a view of the heart (210) with the native mitral valve (220) located between the left atrium, LA (230) and the left ventricle, LV (240). The LVOT (250) directs blood flow from the LV (240) across the aortic valve (260) and into the aorta (265). It is noted that the anterior mitral valve leaflet (160) serves as both a mitral valve leaflet valve function to direct blood flow from the LA (230) to the LV (240) as well as provide one side of the LVOT passage duct during systole. If the anterior leaflet is pushed into the LVOT during systole, blood flow through the LVOT will be restricted resulting in poor patient outcomes.

FIGS. 4A and 4B show one embodiment of the stent-valve frame (270) for use as one portion of a stent-valve (275) the present invention which contains free-edge supported replacement leaflets (280) (or herein also referred to as replacement leaflets) attached to the stent-valve frame (270) in a manner that is similar to the attachment of native mitral leaflets to the mitral annulus (130) and to the cordae tendineae of the body. The stent-valve frame (270) can be formed from a balloon expandable (BE) material such as stainless steel or a self-expanding material such as Nitinol, for example. The wall structure (290) or pattern for the stent-valve frame (270) can be similar to stent patterns used in current vascular stents or current TAVR devices including zig-zag stent structures, closed cell structures, open cell designs, or other stent designs used for stents and stented valves in the vasculature. The waist (300) of the stent-valve frame (270) is that portion of the stent-valve frame (270) that comes into full contact (or approaches full contact) along its entire perimeter with the mitral valve annulus (130) and may also contact a portion of the base of the leaflets; the waist can have a cylindrical shape, a curved shape such as a concave shape (i.e., the waist can curve inwards toward the inside of the stent frame, for example) or it can have a tapered shape such as a surface of a frustum (400). The waist (300) of the stent-valve frame (270) can have a short waist axial length (310) (range 2-5 mm) due to the linear attachment of the leaflets, or the waist can have a longer axial length (310) (range 5-10 mm) such that it can be positioned adjacent to the mitral annulus and other neighboring native valve tissues. The attachment of the leaflet base (550) of the free-edge supported replacements leaflets (540) (see FIG. 5A, for example) of the present invention to the stent-valve frame (270) has a linear attachment along the stent-valve frame perimeter (320) forming a linear replacement leaflet attachment (620) that is an oval or circular attachment to the stent-valve frame (270); the attachment is not crown-shaped.

Various stent-valve frame designs and methods can be used with the present invention to attach the stent-valve frame (270) to the annulus (130) or native mitral valve tissues to prevent migration of the stent-valve frame (270) that houses the free-edge supported replacement leaflets (540). A more detailed description of attachment methods can be found in the patent applications that are referenced herein and are fully incorporated into the present patent application by reference; such attachment methods include suturing, adhesive bonding, solvent bonding, and other attachment methods. Additional examples of attachment designs that are compatible with the present free-edge supported stent-valve frame (270) and free-edge supported replacement leaflets (540) are shown later in this patent specification. The stent-valve frame (270) of the present invention can be a single component stent-valve frame that has the leaflets attached to it and having the stent-valve frame that is attachable directly to the native mitral valve tissue. Alternately, the stent-valve frame (270) of the present invention can be a second component or valve-containing member that is placed into an open central lumen of a first component or support member that is initially placed into the native mitral tissues and attached to the native mitral tissues. The second component is then locked via geometrical fit or via friction to the first component such that the second component is unable to migrate toward the LA (230) or LV (240) as described in further embodiments of this patent application.

Attached to the waist of the stent-valve frame (270) along opposite sides of the waist of one embodiment (FIGS. 4A and 4B), approximately 180 degrees apart from each other along a stent-valve frame perimeter (320) and extending downstream (330) for a distance of 1.5-3 cm are two supports (340) that end in two fastening sites (350), a lateral (or anterior) fastening site (360) and medial (or posterior) fastening site (370). The supports (340) extend inward to a smaller diameter such that the fastening site distance (380) between the lateral fastening site (360) and medial fastening site (370) is smaller than the mitral annulus (130) by several millimeters and smaller (range 5-20 mm smaller) than the waist diameter (390) at the mitral annulus; the supports (340) do not extend into the LVOT as described in FIG. 3 and thereby do not cause any resistance to blood flow out of the LVOT. In an alternate embodiment for the stent-valve frame (270) three supports (340) are attached to the stent-valve frame (270) and extend downstream (330) as shown in FIGS. 4C and 4D. Each of the three supports (340) ends in a separate fastening site (350). Also, as noted in alternate embodiments, the supports (340) can be a portion of the stent-valve frame (270) that extends downstream (330) of the free-edge supported replacement leaflets (280).

Figure 4E:
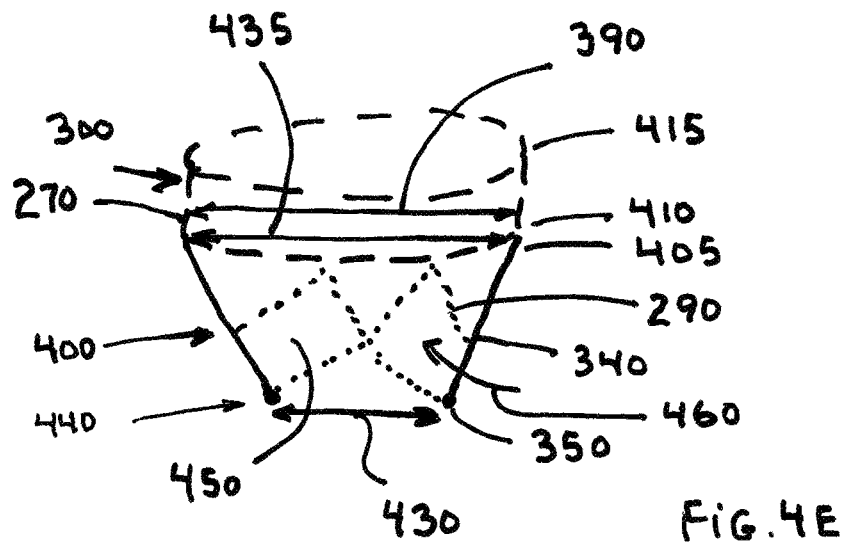
FIG. 4E is a perspective view of the stent-valve frame having two supports that are contiguous with or attached to an expandable frustum frame that extends downstream from the waist.
Figure 4F:
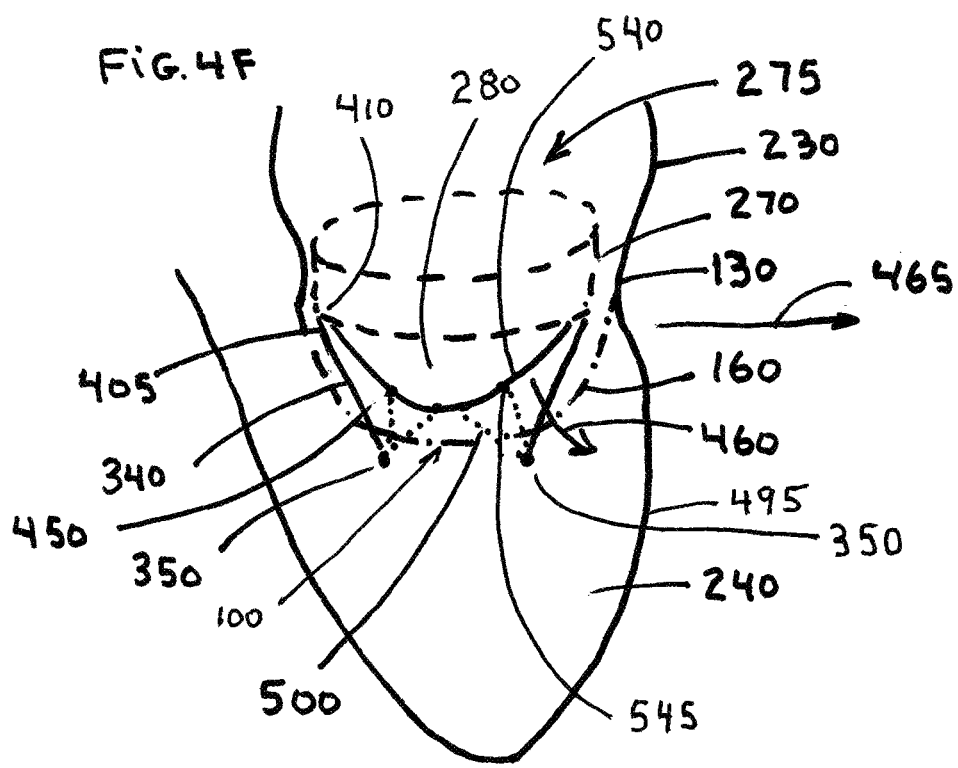
FIG. 4F is a plan view of the stent-valve frame containing replacement leaflets that have free edges that are attached via cords to fastening sites on the supports; the stent-valve frame is positioned with the waist adjacent the mitral annulus.

As shown in FIGS. 4E-4G an upstream end (405) of an expandable frustum portion (400) or frustum (400) of the stent-valve frame (270) is attached to the waist downstream end (410) of the stent-valve frame (270). The expandable frustum (400) can be used to house all or part of the free-edge supported replacement leaflets (280); the replacement leaflets (280) can be attached to and partially housed within the waist of the stent-valve frame. The stent-valve frame (270) of the expandable frustum (400) can also provide the wall structure (290) that serves as the supports (340) or provides an attachment structure for supports (340); the supports therein providing fastening sites (350) which are used to hold the free edges (540) of the free-edge supported replacement leaflets (280). The expandable frustum (400) has a stent-like wall structure (290) formed from a SE or BE material that is similar to that used to form the waist (300) of the stent-valve frame (270) which is located adjacent to the mitral annulus (130). The expandable frustum (400) can be formed such that it is contiguous with the waist or the expandable frustum (400) can be attached to the waist of the stent-valve frame (270) via welding, brazing, sutures, adhesives, or other processing methods and materials used to attach expandable structures such as vascular stents or other implanted medical devices. The expandable frustum (400) forms a smaller frustum outlet diameter (430) (range 5-20 mm smaller) at the frustum downstream end (440) than the waist diameter (390) at the waist downstream end (410). The expandable frustum outlet diameter (430) or frustum downstream diameter (430) is smaller (range 5-20 mm smaller) than the diameter of the mitral annulus or the stent-valve frame diameter (390) that is located within the mitral annulus (130). The expandable frustum (400) does not impinge upon the native or anterior mitral valve leaflet or push the leaflet toward the LVOT and does not cause any restriction in blood flow out of the LVOT (250).

The expandable frustum (400) has a highly open wall structure (450) that allows for blood flow (460) through the stent-like wall structure (290) of the expandable frustum (400) in regions that do not contain a covering. The expandable frustum (400) holds the native mitral valve leaflets (100) outwards (465) and out of direct contact with the replacement mitral valve leaflets (280). The native mitral valve leaflets are provided with blood flow through the open wall structure (450) of the expandable frustum (400) during systole when the replacement leaflets (280) are in a closed configuration (608) (see FIG. 5D, for example). A recirculation space (470) for recirculatory blood flow (480) is maintained between the native mitral valve leaflet and the wall of the LV (240) due to the frustum-like shape of the expandable frustum (400) which has a smaller frustum downstream diameter (430) than the frustum upstream diameter (435) as shown in FIG. 4G. The recirculatory blood flow (480) between the native mitral valve leaflets and the wall of the LV (240) will ensure that blood flow stagnation does not occur and that thromboemboli are not generated. Healing of the native valve leaflets into contact with the outer surface (485) of the expandable frustum (400) can hold the native valve leaflets in a position adjacent to the wall of the frustum (400); such a position will not generate thromboemboli due to recirculatory blood flow (480) and directed blood flow (460) through the open wall structure (450) of the frustum (400). Alternately, the native valve leaflets can continue to flex from a position near the LV lateral wall (495) or within the LVOT (250) during diastole and flex into contact with the frustum shaped frame during systole. FIG. 4F shows a side view of the stent-valve frame (270) positioned adjacent to the annulus and viewing one free-edge supported leaflet (280) that is attached, as a viewing example; the leaflet is attached to fastening sites (350) located at the distal ends (490) of two supports (340) via a plurality of cords (500) that extend from a fastening site (350) on the support (340) to a leaflet attachment site (545) located along a free edge (540) of the replacement leaflet. FIG. 4G shown a side view of the stent-valve frame in a direction perpendicular to that of FIG. 4F; each of the two replacement leaflets (280) are attached via a plurality of cords (500) to both of the fastening sites (350).

The supports (340) can be attached to the expandable frustum (400) or to the waist of the stent-valve frame (270) via welding, soldering, brazing, mechanical attachment methods, adhesives, or other bonding methods. Alternately, the supports (340) can be contiguous with the expandable frustum (400); the wall structure (290) of the expandable frustum (400) can become the supports (340) or serve as the supports. Two or three locations located along the perimeter of the downstream end (440) of the expandable frustum (400) can become the fastening sites (350) to which the cords (500) are fastened; the opposite ends of the cords (500) (opposite to the fastening site ends) are then attached to the free edges (540) of the replacement leaflets (280). Thus, the supports (340), can be formed, for example, by the wall of the expandable frustum (400) and the fastening sites (350) can be specific locations at or near the downstream end of the expandable frustum (400).

As shown in FIGS. 5A-5E the rim (568) of the free-edge supported replacement leaflets (280) are attached at the replacement leaflet base (550) along a linear replacement leaflet attachment (630) that follows a linear path of a circle or oval along a perimeter of a replacement leaflet base (550) attached to the stent-valve frame (270). The stent-valve frame follows the circular or oval shape of the native mitral annulus (130). The rim (568) of the free-edge supported replacement leaflets (280) extends radially inwards to form a free-edge supported anterior replacement leaflet (285) and a free-edge supported posterior replacement leaflet (288). The free edge (540) of the anterior leaflet is attached via a plurality of cords (500) to both the lateral fastening site (360) and the medial fastening site (370) located at the distal end (490) of the supports (340). The free edge (540) of the posterior leaflet is attached via a plurality of cords (500) to both the lateral fastening site and the medial fastening site. The anterior replacement leaflet (285) has a central free-edge region (510) that has a plurality of cords (500) some of which attach to the medial fastening site and some of which attach to the lateral fastening site. The anterior leaflet has an intermediate lateral free-edge region (520) that attaches to the lateral fastening site, for example.

The leaflets of the present invention are formed from pericardial tissue, xenograft heart leaflet tissue, polymeric film, or composite thin members that can function as a heart valve leaflet. A composite leaflet can be formed from a leaflet frame that is embedded or sandwiched within a polymeric or tissue matrix film as described in later embodiments for the leaflet. The leaflet frame be formed of metal or polymeric material and can be attached via the leaflet free edge (540) to cords (500) and the leaflet frame can also be attached along the leaflet base (550) to the stent-valve frame (270) using metal joining methods or polymer bonding methods. FIG. 5B shows a sectional view of the stent-valve frame (270) and supports (340) with the replacement leaflet free edge (540) of the anterior leaflet attached via a plurality of cords (500) to the medial fastening site (370) or lateral fastening site (360). FIG. 5C shows a sectional view (rotated by 90 Degrees from FIG. 5B) of the stent-valve frame (270) with the anterior replacement leaflet (285) and posterior replacement leaflet (288) in an open configuration (606) such as found during diastole. The anterior replacement leaflet is attached at the replacement leaflet base (550) to the inlet end (405) or upstream end (405) of the frustum (400). FIG. 5D shows a sectional view (rotated by 90 Degrees from FIG. 5B) of the support structure with the anterior replacement leaflet (285) and posterior replacement leaflet (288) in a closed configuration (608) such as found during systole. FIG. 5E shows a perspective view of the anterior replacement leaflet (285) attached via a central free-edge region (510) and an intermediate free-edge region (520) to a medial fastening site (370) and a lateral fastening site (360).

FIGS. 6A and 6B shows an embodiment of a stent-valve frame (270) that has two fastening sites (350) that are intended to provide attachment of cords (500) (shown in FIGS. 5A-5E) that attach to replacement leaflet free edge (540) of a bicuspid valve having free-edge supported replacement leaflets (280) as described in FIGS. 5A-5E. In this embodiment, the two fastening sites (350) are attached together via a lateral support member (560) or lateral support arm. The medial support member holds the medial fastening site (370) at a specific fastening site distance (380) from the lateral fastening site (360) and provides structural stability to the supports (340). The fastening site distance is smaller (range 5-20 mm smaller) than the diameter of the mitral annulus (130) and smaller (range 5-20 mm smaller) than the waist diameter (390) of the stent-valve frame (270) that is located in the annulus. Other stent-valve frame structures are anticipated that provide fastening sites (350) located downstream (330) of the mitral annulus (130) and downstream (330) of the replacement leaflets (280) to hold cords (500) that attach to the replacement leaflet free edges (540). An expandable frustum (400) may be attached to the waist of the stent-valve frame (270) that is described in FIGS. 6A, 6B, 5A-5E, and in FIGS. 4E-4G, the supports (340) can be independent from the frustum (400) stent-valve structure or the supports (340) can be attached or contiguous with the frustum stent-valve wall structure (290). Alternately, as described in earlier embodiments, the supports (340) can be attached to and extend downstream (330) from the waist (300) to a location distal to the replacement leaflet free edge (540) for attachment of the replacement leaflet free edge (540) via cords (500) without the presence of a frustum-shaped frame (400).

FIG. 7 shows an embodiment for a stent-valve frame (270) for a stent-valve (275) having a support (370) that is attached to the waist (300) of a stent-valve frame (270) via an upper support member (562) and a central shaft (565) that extends downstream (330) of the stent-valve frame (270) along a centerline (564) of the stent-valve frame to a location downstream (330) of the free edge (540) of the replacement leaflets (280). One or more fastening sites (350), attached directly to the central shaft (565) via a lower support arm (566), are attached to cords (500) that then attach to the free edge (540) of free-edge supported leaflets. Alternately, a single central shaft (565) can extend along a centerline (564) of the stent-valve frame (270) to a central site (567) downstream (330) of the replacement leaflets (280). One, two, three, or more fastening sites (350) attached directly or indirectly to the central site (567) of this central shaft (565) can be used to hold cords (500) that are then attached at the opposite ends of each of the cords (500) to the free edges (540) of the replacement leaflets (280).

Figure 8A:
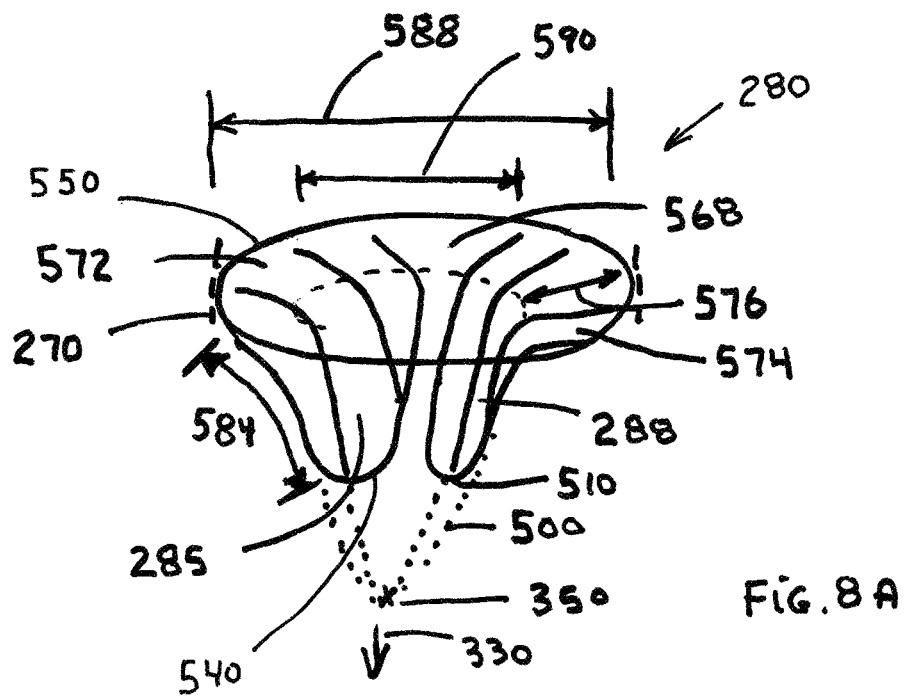
FIG. 8A is a perspective view of anterior and posterior replacement leaflets having a rim that extends from the anterior and posterior replacement leaflet cusps to the rim outer diameter; the anterior and posterior cusps are shown attached via cords to one of the fastening sites.
Figure 8B:
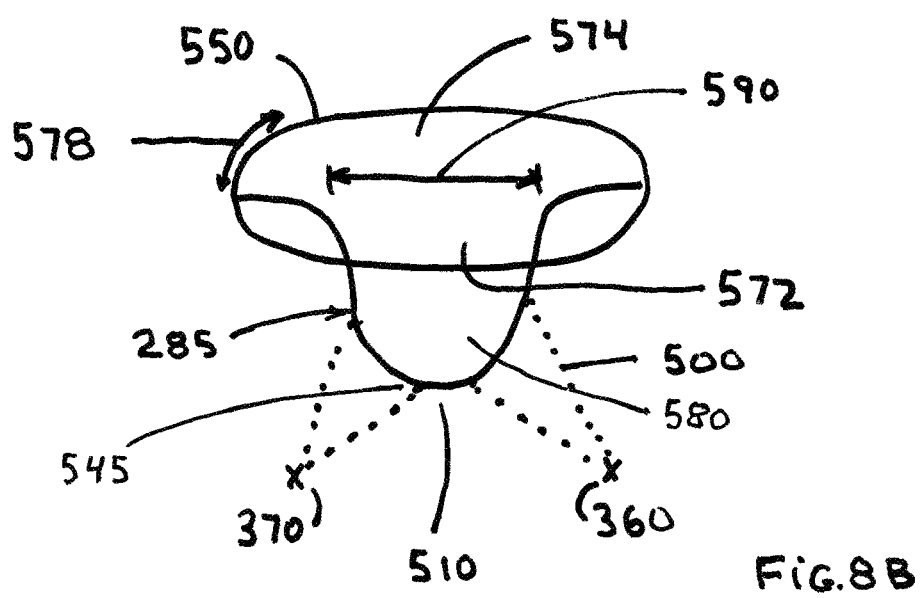
FIG. 8B is a perspective side view of replacement leaflets of FIG. 8A in a direction perpendicular to FIG. 8A showing the free edge of the anterior leaflet attached to both the medial and lateral fastening sites.

The valve leaflet assembly (280) or replacement leaflets (280) are comprised of the leaflet rim (568) plus the leaflet cusps; for the present invention the leaflet assembly (280) can be comprised of two leaflets, three leaflets, or more than three leaflets; each leaflet being comprised of a portion of a replacement leaflet rim (568) plus a replacement leaflet cusp (570) (see FIGS. 8A-8B). As shown in FIGS. 8A-8C this valve embodiment contains two leaflets, an anterior leaflet (285) and a posterior leaflet (288) that are supported along the replacement leaflet free edges (540) by cords (500) which are attached via leaflet attachment sites (545) to one end of the cords; the opposite ends of the cords (500) are attached to fastening sites (350). Each leaflet of the present embodiment and other embodiments of the present invention is attached to at least one cord but preferably is attached to 2 or more cords (500). The cords (500) of the present invention can be constructed from a polymeric fiber such as polytetrafluoroethylene (PTFE), polyethylene terephthalate (PET) or other strong, high tensile strength, flexible, biocompatible fiber formed via a monofilament or multifilament structure; alternately, the cord can be formed from metal strands formed from stainless steel, for example, or composite strands including multifilament strands.

The central free edge regions (510) for the anterior replacement leaflet cusp (580) is attached to a lateral fastening site (360) and a medial fastening site (370). Similarly, the posterior replacement leaflet cusp (582) is attached to a lateral fastening site and a medial fastening site. The anterior replacement leaflet (285) has an anterior rim (572) that is contiguous with and forms a portion of the anterior replacement leaflet; the anterior rim is contiguous with the anterior replacement leaflet cusp (580). The replacement leaflet base (550) is attached to the stent-valve frame (270) via attachment means which include sutures, adhesive bonding, and other attachment means known in the industry. The posterior replacement leaflet has a posterior rim (574) that is contiguous with and forms a portion of the posterior replacement leaflet (288); the posterior rim (574) is contiguous with the posterior leaflet cusp (582); the posterior rim extends to the leaflet base (550) that is attached to the stent-valve frame (270). The anterior rim (572) and the posterior rim (574) form a leaflet assembly rim or replacement leaflet rim (568) that extends with a rim width (576) around the entire perimeter of the valve leaflet assembly forming the perimeter of the replacement leaflet base perimeter (578). The anterior leaflet cusp (580) is separated from the posterior leaflet cusp (582) forming a separate replacement leaflet cusps (570) downstream (330) from the leaflet assembly rim. The rim width for the present invention is 4 mm (range 2-10 mm). The replacement leaflet length (584) for the anterior leaflet or posterior leaflet extending along an integrated path from the attachment of the leaflet to the stent-valve frame (270) at the leaflet base to the leaflet central free-edge region (510) is 2 cm (range 1.5-2.5 cm). The rim outer diameter (588) located at the attachment of the rim (568) with the stent-valve frame (270) is equal to the diameter of the stent-valve frame; the stent-valve waist diameter (390) is equal to the diameter of the mitral valve annulus or native valve tissues to which the stent-valve frame (270) is attached; the mitral annulus (130) is typically 35 mm in diameter (range 28-45 mm). The rim inner diameter (590) at a location between the leaflet assembly rim (568) and the anterior/posterior cusps is 8 mm smaller (range 4-20 mm smaller) than the outer rim diameter. The replacement leaflet rim (568) serves to provide a continuous layer of leaflet material that is impermeable to blood flow and that provides a seal to prevent blood regurgitation near the perimeter of the anterior replacement leaflet (285) and posterior replacement leaflet (288) during leaflet coaptation in systole. The free edge supported replacement leaflets (280) of the present invention are not required to have a rim (568); the leaflets cusps can extend to the leaflet base and attach to the stent-valve frame (270). The leaflet assembly for the embodiment of a bicuspid valve can be seen splayed out flat in FIG. 8C. The individual valve leaflets as shown are attached to two fastening sites (350), the lateral fastening site (360) and the medial fastening site (370); additional fastening sites (350) can be designated for a valve leaflet if desired. FIG. 8D shows a tricuspid valve leaflet assembly of the present invention in a splayed out manner. The tricuspid valve assembly contains three fastening sites (350) as shown in this embodiment, although additional fastening sites (350) can be provided without deviating from the present invention.

One important aspect of the present invention is the structure of the stent-valve (i.e., stent-valve frame plus replacement leaflets (280) needed to ensure that the replacement leaflets (280) of the present invention are readily closed during the high pressure systolic cycle of LV (240) heart contraction; additionally the replacement leaflets (280)

should not provide regions of blood stagnation that could lead to thrombus formation. FIGS. 9A and 9B show an embodiment of the stent-valve (275) placed with the stent-valve frame (270) adjacent the mitral annulus (130). The native mitral leaflets (100) and the replacement leaflets (280) are shown in an open configuration (606) allowing blood to flow downstream (330) through the valve during diastole in FIG. 9A. The replacement leaflets (280) are held by cords (500) which are attached to fastening sites (350) located on the stent-valve frame (270) which can serve as the supports (340) or to supports (340) which can be attached as supports (340) to the stent-valve frame (270) as described earlier. During systole (see FIG. 9B) as blood pressure is increasing the replacement leaflets (280) of one embodiment having a longer replacement leaflet length (584) than the native leaflet length (586) (extending from the mitral annulus (130) to the native leaflet free edge (150)) are forced into a closed configuration (608). The replacement leaflet length (584) of this embodiment are 4 mm longer (range 2-8 mm longer) than the native leaflet length (586) or are positioned with a portion of the replacement leaflet free edge (540) downstream (330) of the native leaflet free edge (150) to ensure that blood pressure within the LV (240) is acting on an exposed area (592) of the replacement leaflets (280) that cannot be blocked by the native leaflets even if the native leaflets are oriented directly adjacent to the replacement leaflets (280). The stent-like structure of the expandable frustum (400) will hold the native leaflet outwards (465) during systole as the native leaflet is pushed into contact with the frustum (400) due to the LV (240) blood pressure. The frustum length (594) is longer than the replacement leaflet length (584) to provide a fastening site (350) at a location downstream (330) from the replacement leaflet free edge (540) from which a cord can be attached from the fastening site (350) and the opposite end of the cord attached to the leaflet central free edge region (510) of the replacement leaflet (280).

Figure 10A:
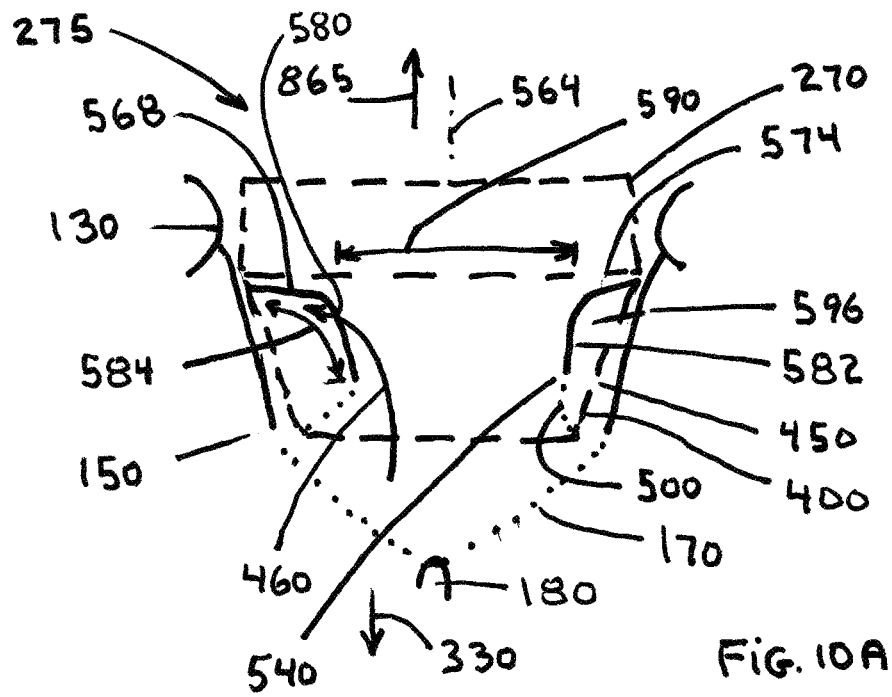
FIG. 10A is a plan side view of the stent-valve frame having replacement leaflets attached to the stent-valve frame and in an open configuration; the replacement leaflets have a rim that provides an open space for blood flow and blood pressure access.
Figure 10B:
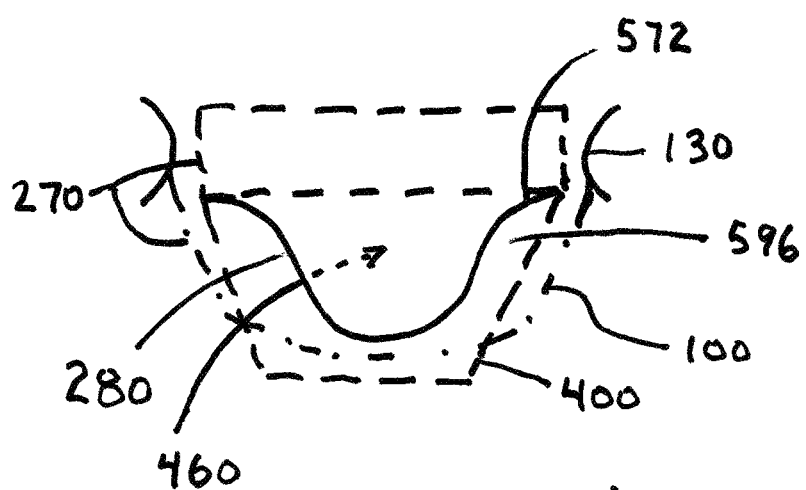
FIG. 10B is a plan side view of the stent-valve frame showing an anterior replacement leaflet attached and in a closed configuration; the replacement leaflets have a rim that provides an open space for blood pressure access during systole to close the replacement leaflets.

In other embodiments the replacement leaflets (280) have the same replacement leaflet length (584) as the native leaflet length (586) and can alternately be smaller in replacement leaflet length (584) than the native leaflet length (586). An alternate embodiment for the stent-valve (275) including the leaflet assembly (280) is shown in FIGS. 10A and 10B. In this embodiment the replacement leaflet rim (568) is formed such that it is attached to the waist but does not make contact (along most of the perimeter) with the wall structure (290) of the expandable frustum (400). In this embodiment the replacement leaflet length (584) is similar or shorter than the native leaflet length (586) extending from the annulus (130) to the native leaflet free edge (150). The leaflet assembly rim (568) extends from its attachment to the waist (300) of the stent-valve frame (270) inwards toward the device centerline axis (564) for a distance equal to the rim width (576) to reach the rim inner diameter (590). Located farther downstream (330) of the replacement leaflet rim (568) are the replacement leaflet anterior cusp (580) and replacement leaflet posterior cusp (582). Blood flow (460) and blood pressure during systole will always have an open pathway to deliver high pressure blood through the open wall structure (450) of the expandable frustum (400) and into the open space (596) that is located between the expandable frustum and the replacement leaflets (280) and thereby closing the replacement leaflets (280) during systole. FIG. 10B shows the stent-valve in a lateral view that is 90 degrees out of phase from FIG. 10A; the blood pressure and blood flow path (460) into the open space (596) cannot be blocked even if the native valve leaflets (100) are aligned adjacent to the replacement valve leaflets (280).

Figure 11:
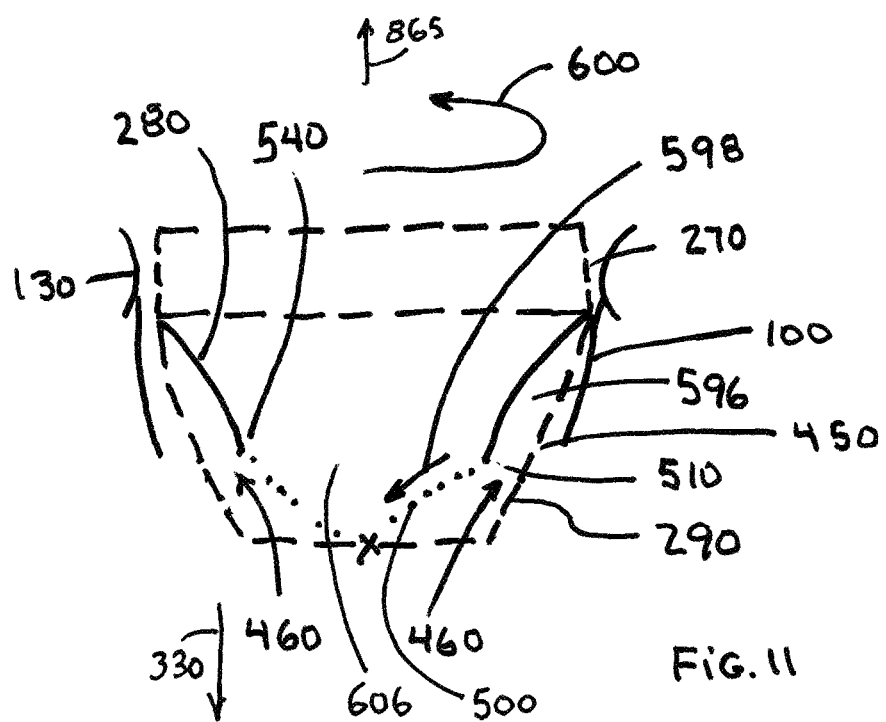
FIG. 11 is a plan side view of the stent-valve frame showing the free edges of the replacement leaflets attached via cords to one of the fastening sites such that the free edges are held away from the native leaflet and providing an open space for blood pressure to act upon the replacement leaflets for ensuring closure during systole.

In a further embodiment shown in FIG. 11, the replacement leaflets (280) are held by the cords (500) such that the replacement leaflets (280) do not come into contact with the stent-like wall structure (290) of the expandable frustum (400) as shown during diastole when the replacement leaflets (280) are in an open configuration (606). Cords (500) attached to the leaflet central region (510) on one end of each of the cords and attached to the fastening sites (350) on the opposite end of the cords (500) hold the leaflet free edge (540) of this embodiment with a tension (598) that does not allow the replacement leaflets (280) to contact the wall structure (290) of the expandable frustum (400) during diastole. In this embodiment during systole, the blood flow (460) and blood pressure will always have a direct path through the open wall structure (450) of the expandable frustum (400) to the downstream (330) side of the replacement leaflets (280) to the open space (596) to provide a pressure force against the replacement leaflets (280) to drive the replacement leaflets closed and into coaptation (or contact of the leaflet cusps) with each other. The native leaflets (100) cannot block the blood flow (460) from reaching the downstream (330) side of the replacement leaflets (280) even if the native leaflets are positioned identically adjacent to the replacement leaflets (280). Thus the stent-valve frame (270) of the present invention is not required to be oriented in a circumferential direction (600) as the stent-valve frame is positioned within the native annulus (130) and native tissues of the native heart valve.

It is understood that embodiments that lengthen the replacement leaflet length (584) or form an open space (596) between the replacement leaflets (280) and the expandable frustum (400) as described in previous embodiments are not necessary if the operator is willing to orient the replacement leaflets (280) of the present invention such that the replacement anterior leaflet (285) is not placed adjacent to the native anterior leaflet (160) and the replacement posterior leaflet (288) is not placed adjacent to the native posterior leaflet (165). Such orientation of the stent-valve of the present invention will allow blood flow and blood pressure to have a direct pathway to the downstream (330) side of the replacement leaflets (280) during systole and allow the replacement leaflets (280) to close properly. Furthermore it is understood that the high blood velocity extending in a retrograde or upstream (865) direction (i.e., opposite to downstream (330) direction) through the open replacement leaflets (280) of the stent-valve of the present invention at the start of systole will be associated with a low pressure (via energy conversion described by Bernoulli Equation) that will have a tendency to pull the replacement leaflets (280) of the present invention into a closed configuration (608) during systole without the need for a length increase (relative to the native leaflet length) for the replacement leaflet length (584) or creating a presence of an open space (596) as presented herein.

The replacement leaflets (280) for the present invention can be formed from tissues taken from animal pericardium, xenograft heart valve, allograft heart valve, or other tissue or collagen materials. Alternately, the replacement leaflets (280) can be formed from a thin layer of polymeric material such an expanded polytetrafluoroethylene (ePTFE), Dacron film, polymeric woven, braided, or knitted material. Alternately, polymeric material, collagen tissue, and other tissue material can be used by themselves or in combination with other materials including and embedded leaflet frame or embedded fibers to form a composite replacement leaflet of the present invention. Often a polymeric or tissue material that is exposed to continued stress will tend to creep, therefore many of the polymeric films and some of the tissue or collagen materials used for valve leaflets will need to be supported by fibers or films made from stronger materials that will not creep under stress. Also support fibers or films can be used to provide attachment strength to the replacement leaflet such that the leaflet does not break or tear under stresses from blood pressure or form a leakage site. Such stronger support fibers and films include Dacron fibers, thin multifilament metal fibers, thin metal films such as Nitinol films and other materials of similarly high tensile strength and low creep; such films and fibers can have diameters and thickness of 0.001 inches (range 0.0003-0.002 inches) and can be very flexible.

Figure 12A:
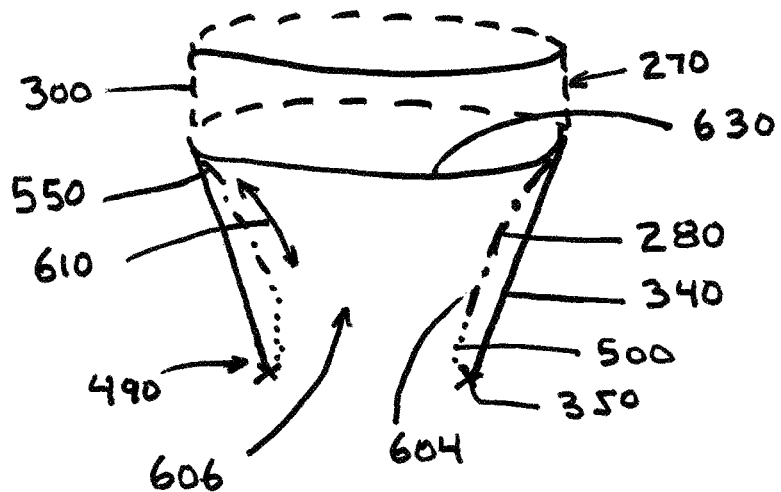
FIG. 12A is a perspective side view of the free-edge supported replacement leaflets in an open configuration being attached along the leaflet base to the stent-valve frame and attached via the free edges to fastening sites via cords.
Figure 12B:
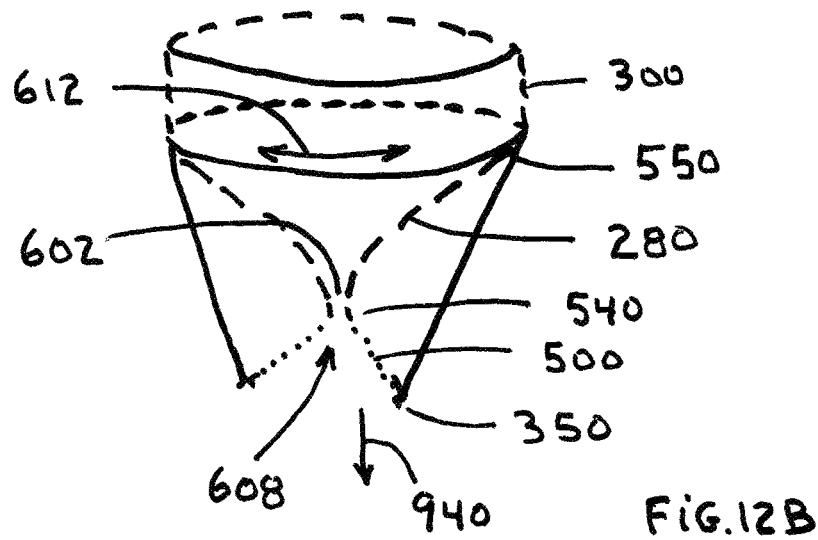
FIG. 12B is a perspective side view of the free-edge supported replacement leaflets in a closed configuration with the leaflets making contact with each other forming a coaptation surface.

The replacement leaflet base (550) of the free-edge supported valve leaflets of the present invention is attached to the wall of a stent-valve frame (270) in a linear replacement leaflet attachment path (630) that is a round circle or oval as shown in FIG. 12A. The replacement leaflet free edge (540) of the replacement leaflet (280) comes into direct contact with a neighboring leaflet cusp (570) and a portion of the valve leaflet coapts with the neighboring leaflet forming a coaptation surface (602) or coaptation region in a closed leaflet configuration (608) as shown in FIG. 12B. The free edges (540) of each of the leaflets are attached via cords (500) to two fastening sites (350) as described in earlier embodiments; the fastening sites are located at the distal ends (490) of two supports (340) that are attached to the stent-valve frame as described in earlier embodiments of the present invention or the fastening sites form a local region of the stent-valve frame. The supports (340) can extend along two or more sides of a frustum-shaped housing along the length of the frustum (400) and form fastening sites (350) for the cords (500) at their downsteam ends. The supports (340) can also attach to a waist of the stent-valve frame and extend distally (940) to the fastening sites (350) without the frustum stent-valve frame.

Figure 12C:
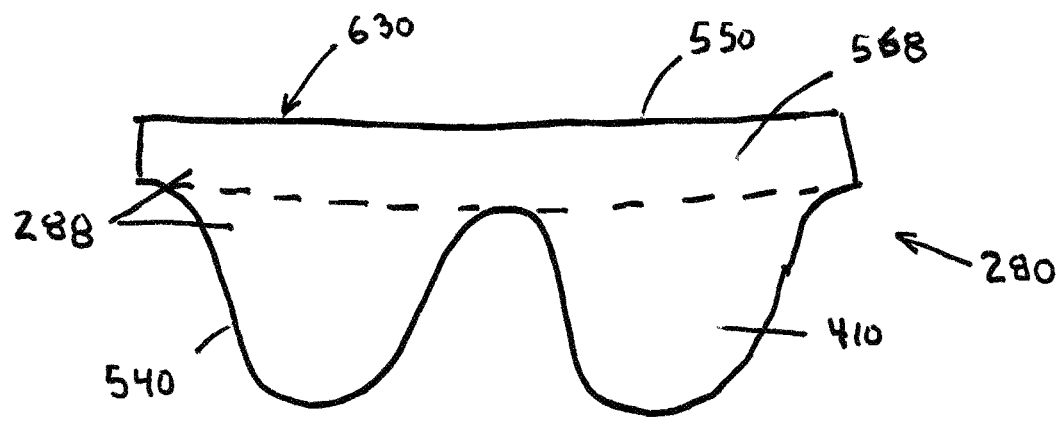
FIG. 12C is a plan view of bicuspid replacement valve leaflets identifying the free edge and the linear attachment path of the leaflet that is made with the stent-valve frame.
Figure 12D:
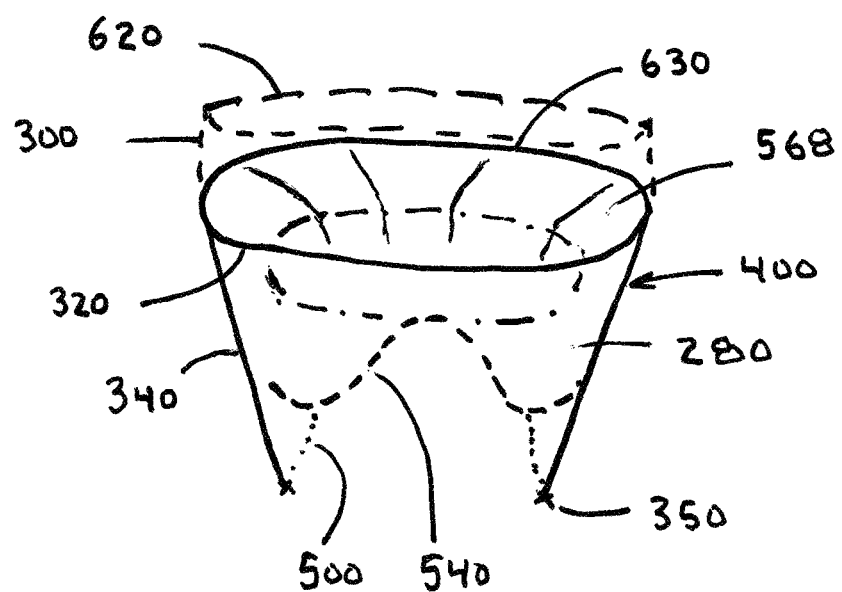
FIG. 12D is a perspective view showing the linear attachment path of the leaflet base with the stent-valve frame and the attachment of the free edges to attachment sites via cords.

The replacement leaflet surface (604) changes shape as the leaflet moves from an open configuration (606) as shown in FIG. 12A to a closed configuration (608) as shown in FIG. 12B. The leaflets flex via extension in both the axial flex direction (610) and the circumferential flex direction (612) as they move from an open position to a closed position. The axial flexibility characteristics for the leaflet can differ from the circumferential flexibility characteristics by altering the material and dimensions for the axial fibers relative to the circumferential fibers. Leaflet support fibers can be located within the wall structure of polymeric or tissue leaflets to allow leaflet expansion to occur in a controlled manner and with a controlled leaflet shape; also, support fibers provide an attachment region by which the replacement leaflets (280) can be attached to the stent-valve frame (270) of the present invention; also, the support fibers strengthen the free edge (540) of the leaflets to prevent the free edge (540) from encountering irreversible stretching. An embodiment for two free-edge supported leaflets or leaflet cusps that are found as replacement leaflets (280) in the present free-edge supported stent-valve device is shown in a splayed-out manner in FIG. 12C. The linear replacement leaflet attachment path (630) for attached edge or replacement leaflet base (550) of the leaflets is shown; the linear attachment path can be attached to the stent-valve frame along the waist perimeter (620) or other stent-valve frame perimeter (320) via a variety of attachment means including sutures, adhesives, and other attachment means. Although the present invention is described for two free edge supported replacement leaflets, the free-edge supported stent-valve of the present invention can be formed with three or four leaflets, instead of two, for example, without deviating from the present invention.

Figure 13A:
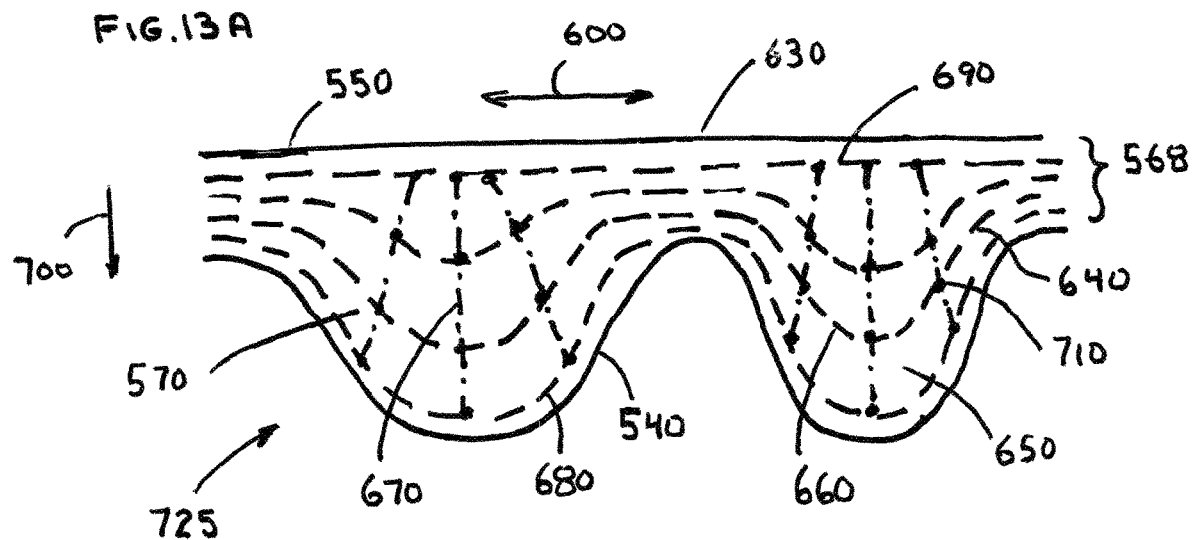
FIG. 13A is a plan view of a bicuspid replacement valve leaflets splayed out on a flat surface; the leaflet are formed from polymeric or tissue matrix material and have fibers embedded or attached that extend in a circumferential and axial direction.
Figure 13B:
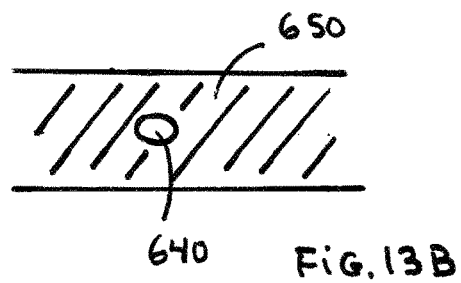
FIG. 13B is a plan view showing a fiber embedded in a polymer or tissue matrix.
Figure 13C:
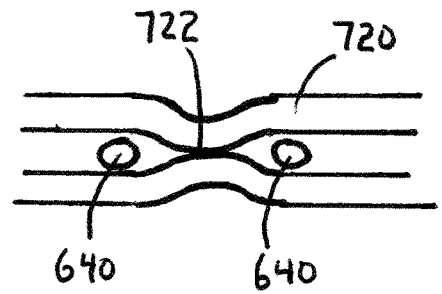
FIG. 13C is a plan view showing a fiber sandwiched between two film layers of polymer material or tissue matrix material.

One embodiment for the free-edge supported replacement leaflets (280) of the present invention is shown in FIG. 13A-13C. This replacement leaflet (280) is formed from a polymeric film or tissue matrix that is formed via either a film casting process, an extrusion process, or other film forming process. In this embodiment fibers (640) formed from Dacron, Nitinol, stainless steel or other high tensile and low-creep material, for example, are embedded within the polymer or tissue matrix (650) of the leaflet polymeric or tissue matrix film, such as polyurethane, collagen, acellular matrix, or cellular tissue, for example, as shown in FIGS. 13A and 13B. The fibers include circumferentially oriented fibers (660) and axially oriented fibers (670). A free-edge fiber (680) can extend along the free edges (540) of the replacement leaflets (280) in a circumferential direction (600); an attachment-edge fiber (690) can extend along the attached edge or replacement leaflet base (550) of the leaflets in a circumferential direction. One or more axial fibers (670) can extend with a substantial axial componency in the axial direction (700) from the free-edge fiber to the attachment-edge fiber. Axial fibers (670) can be attached to free-edge fibers (680) or attachment-edge fibers (690) at fiber attachment sites (710) via brazing, soldering, welding, adhesives, or other bonding methods. The circumferentially oriented fibers (660) and axially oriented fibers (670) can be embedded within the polyurethane or tissue matrix (650); the polymer matrix or tissue matrix can be solvent cast or thermally cast around the fibers (640) as shown in FIG. 13B. Alternately, two separate films (720) of polyurethane or tissue material can be placed onto each side of the fibers (640) and heated to thermally bond the two film layers together or bonded together via adhesives, solvent bonding, or other bonding method around the fibers to form a sandwich of the polymer or tissue film on each side of the fibers forming a film bond (722) as shown in FIG. 13C.

Figure 13D:
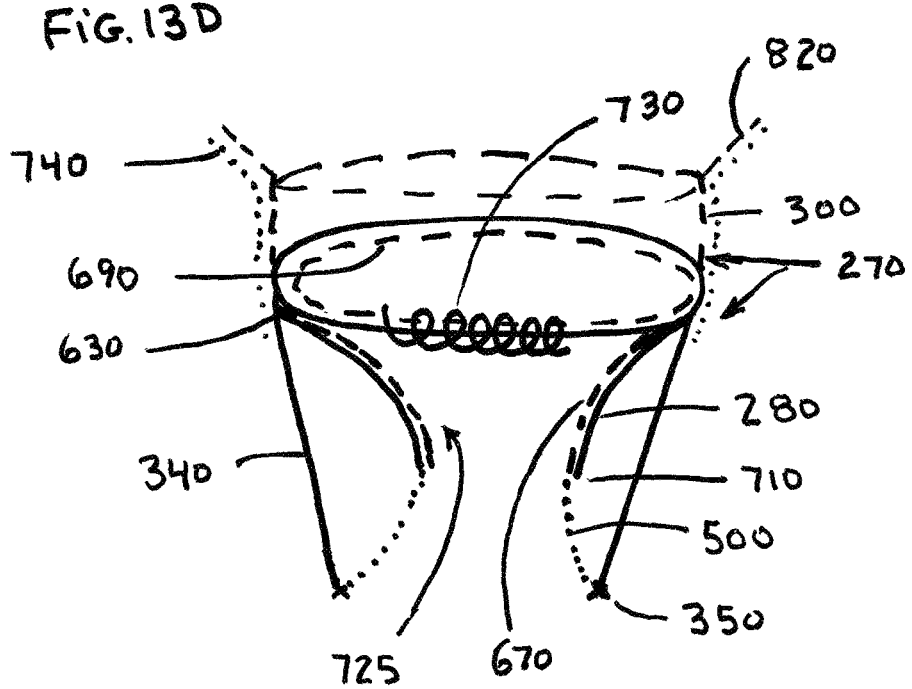
FIG. 13D is a perspective view of the stent-valve frame attached to the fiber-embedded polymeric or tissue matrix replacement valve leaflets; sutures can attach the replacement valve leaflet to the stent-valve frame; cords can attach to the free edges of the replacement leaflets.
Figure 13E:
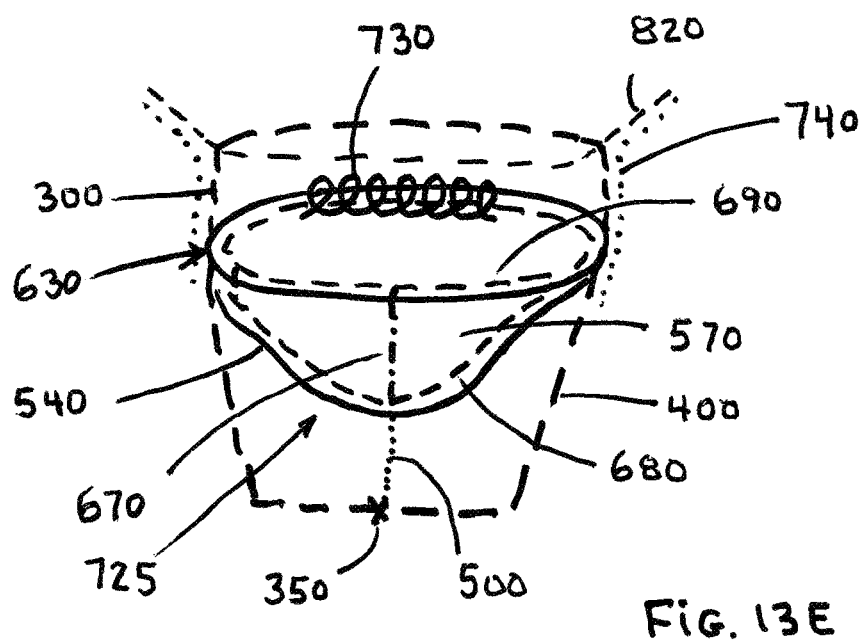
FIG. 13E is a perspective side view of one fiber-embedded replacement valve leaflet shown in a direction perpendicular from FIG. 13D.

The polymer (or tissue) and fiber composite replacement leaflets (725) can then be attached to the waist (300) or to the stent-valve frame (270) via a variety of methods. Sutures (730), for example can be used to sew the attachment-edge fiber (690) to the stent-valve frame (270) as shown in FIGS. 13D and 13E; FIG. 13D is a side view of the stent-valve and FIG. 13E is a side view that is perpendicular to the view of FIG. 13D showing the composite replacement leaflet (725) attached to the stent-valve frame (270) of the present invention. Alternately, the polymer or tissue matrix used as the leaflet film can be used also as a covering (740) for the stent-valve frame (270). A covering (740) is attached to the stent-valve frame (270) of the present invention to cover a portion of the stent-valve frame to prevent blood leakage past the stent-valve from the LV (240) to the LA (230). The waist (300), upper bulb (820) and a portion of the frustum (400) of the stent-valve frame (270) can have a covering (740) attached to it. The polymer or tissue matrix of the composite replacement leaflet can be thermally joined, solvent bonded, adhesively bonded, or otherwise attached to the stent-valve frame covering (740). Other materials can be used as a covering (740) material including but not limited to expanded polytetrafluoroethylene (ePTFE), polyethylene terephthalate, Dacron, and Nylon films and weaves of fibers formed from such polymer materials.

The composite replacement leaflet (725) can be joined to the stent-valve frame forming a linear attachment (630) via polymer to polymer (or matrix to matrix) bonding methods which include thermal bonding, solvent bonding, adhesive bonding, and other forms of bonding. The replacement leaflet free edges (540) can be attached to cords (500) at the fiber/edge attachment site (710); the cords (500) are then attached at their opposite ends to fastening sites (350); the cords (500) thereby functioning to prevent eversion of the leaflets in a direction towards the LA during systole. Attachment of the cords (500) to the fiber/edge attachment sites (710) can be performed via forming a loop or knot made with sutures, for example, around the fibers that form the fiber attachment site, using adhesives, brazing, thermal bonding, or other methods available. The cords (500) can be formed from polymeric or metallic monofilament or multifilament strands; the cords (500) can be attached to the fastening sites (350) using adhesives, sutures, forming a loop, and other bonding methods.

Figure 14A:
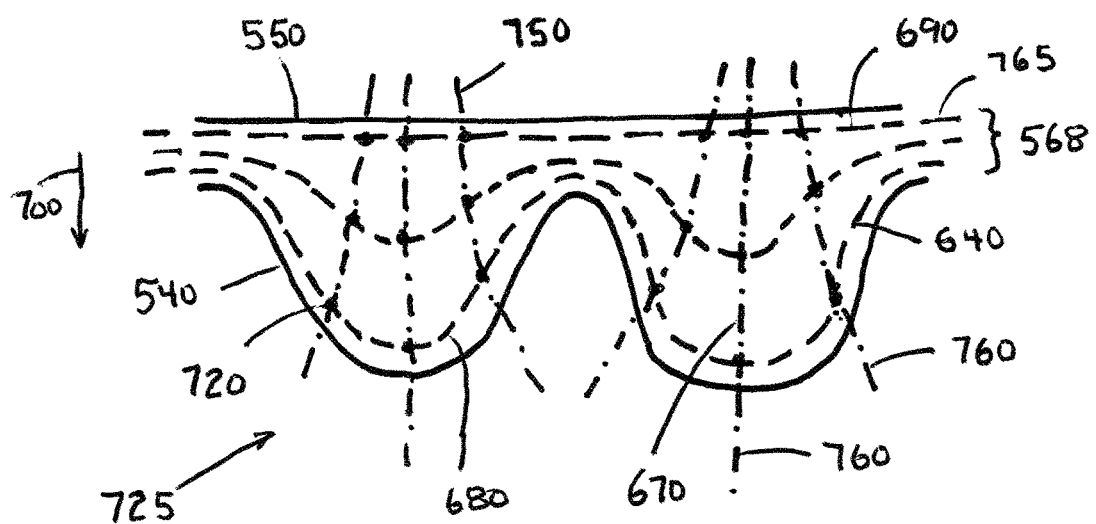
FIG. 14A shows a plan view of splayed bicuspid replacement valve leaflets having embedded fibers that extend outwards in an axial direction beyond the leaflet base for attachment to the stent-valve frame and extend beyond the free edges for attachment to the fastening sites.
Figure 14B:
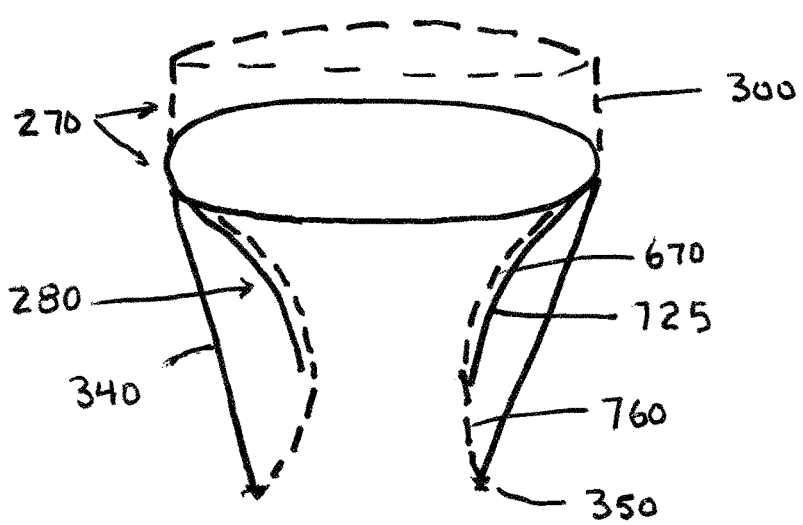
FIG. 14B is a perspective view of the stent-valve frame having fiber-embedded replacement leaflets that extend in an axial direction for attachment to the stent-valve frame and for attachment to the fastening sites.

Another embodiment for attaching the polymer or tissue matrix and fiber composite replacement leaflets (725) to the stent-valve frame (270) is shown in FIGS. 14A-14B. In this embodiment the axial fibers (670) are allowed to extend beyond the attached-edge fiber (690) forming an attached edge extension fiber (750) as shown in FIG. 14A. The attached-edge extension fiber (750) can then be attached directly to the stent-valve frame (270) via brazing, welding, swaging, adhesive bonding or other bonding methods available; the axial fibers (670) can alternately be formed to be contiguous with the stent-valve frame (270). The axial fiber (670) can extend beyond the free edge fiber (680) forming a free-edge extension fiber (760). The circumferential fibers (660) can extend beyond the edge of the polymer matrix of the composite replacement leaflet (725 forming circumferential extensions (765) that can be used form the composite leaflet (725) into a circular shape or to attach the composite leaflet (725) to the stent-valve frame (270). The free-edge extension fiber (760) can be attached directly to the cords (500) via forming a knot, weld, or adhesive bond; alternately, the axial fiber free-edge extension (760) can extend all the way to the fastening site (350) where it is attached to the fastening site (350) via brazing, adhesive bonding, swaging, forming a loop or knot, or other attachment methods as shown in FIG. 14B.

A thin film of Nitinol or other metal, or other leaflet frame film (775) can be cut via laser, electric discharge method (EDM) or other methods to form a leaflet frame (770) that is splayed out as shown in FIG. 15A; the circumferential members (780) of the leaflet frame (770) are then formed into a circular shape and attached to the waist (300) of the stent-valve as shown in FIG. 15B. The leaflet frame can have axial members (790) and circumferential members (780); the circumferential members can extend along the free edge (540) forming free-edge members (800) and along the attached edge forming attachment edge members (810); axial members can extend from the free-edge members to the attached-edge members and can be contiguous with them. The leaflet frame can be embedded within a polymer or tissue matrix as described earlier for the fiber supported composite replacement leaflet (725), alternately the leaflet frame can be sandwiched between to polymer films or tissue matrix films via thermal, solvent, adhesive, other bonding method used to bond two films together. The leaflet frame (770) of the composite leaflet (725) can be attached to the stent-valve frame (270) via sutures, adhesive bonding, thermal bonding, welding, brazing, soldering, or other methods as described for the polymeric film or tissue matrix that contained fibers embedded or sandwiched within its wall thickness. Alternately, the leaflet frame can be contiguously formed along with the stent-valve frame (270), the leaflet frame extending without discontinuity from the replacement leaflet (280) to the stent-valve frame (270).

The free-edge supported replacement valve leaflets of the present invention are intended to be attached to an expandable stent-valve frame (270) that is used as a transcather mitral valve replacement (TMVR) device. The stent-valve has a waist frame (270) located adjacent the annulus (130), an upper bulb (820) can be attached to the waist and located in the LA (230), and a frustum-shaped housing (400) can be attached to the waist and located downsteam from the waist in the LV (240) as shown in FIG. 15B. A covering (740) material formed from a thin polymeric or tissue matrix film or a thin woven fabric can be attached to the upper bulb (820), the waist (300), and other portions of the stent-valve frame (270) to ensure that blood is not allowed to pass from the LV (240) to the LA (230) when the replacement leaflets (280) are in a closed configuration (608) as is found during systole for a mitral valve.

The stent-valve frame (270) containing the free-edge supported leaflets of the present invention can be a single member stent-valve (830) wherein the stent-valve frame (270) that contains the replacement leaflets (280) is attached directly to the native mitral valve tissues. The stent-valve frame can be attached to the mitral valve tissues using any attachment method or design that is currently being used or anticipated for use in attaching a stent-valve frame (270) to the mitral annulus, mitral leaflets, heart myocardium, or other native tissues of the heart for TAVR or TMVR procedures.

Figure 16A:
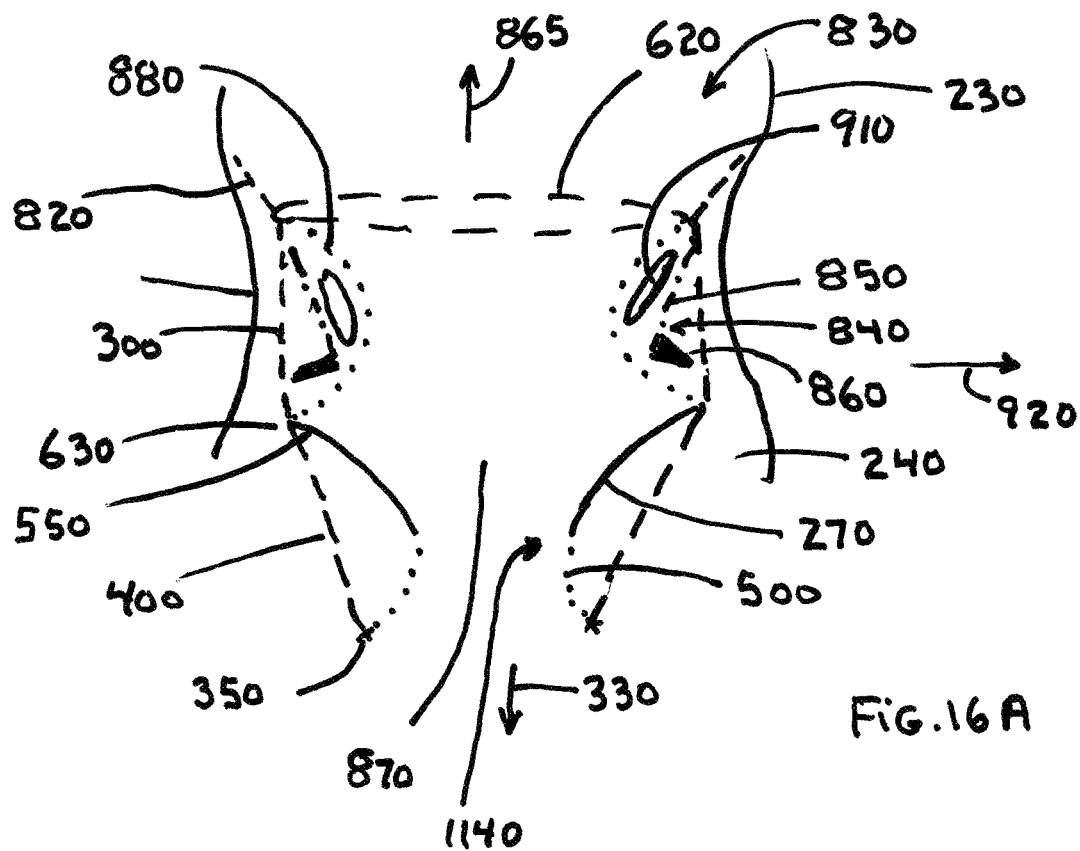
FIG. 16A is a plan side view of a single component stent-valve having an attachment mechanism to the mitral valve annulus that contains barbs in an inactive configuration located adjacent an uninflated torus balloon; the stent-valve frame has the base of the replacement leaflet attached to the stent-valve frame in a linear configuration and the leaflet free edges are attached to supports via cords.
Figure 16B:
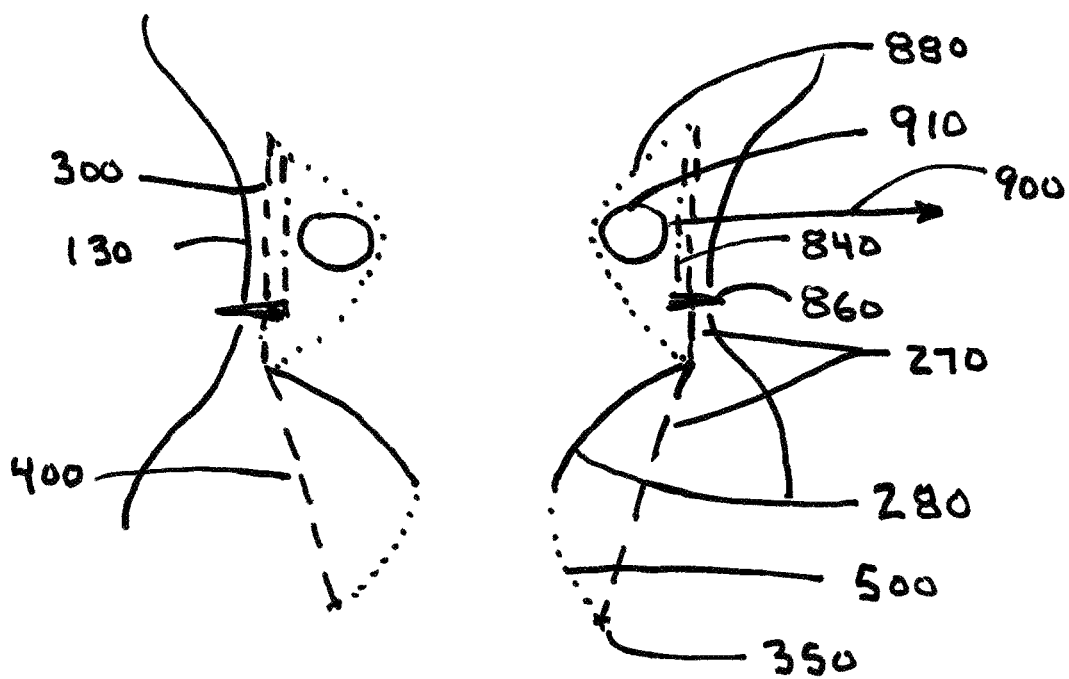
FIG. 16B is a plan side view of a single component stent-valve having an attachment mechanism to the mitral valve annulus to prevent migration of the stent-valve frame that contains barbs in an active configuration located outside of the stent-valve frame due to inflation of a torus balloon; the stent-valve frame has the base of the replacement leaflet attached to the stent-valve frame in a linear configuration and the leaflet free edges are attached to supports via cords.

The waist of one embodiment of the present stent-valve frame can be attached to the annulus (130) via a series of 16 barbs (840) (range 8-20) located along the perimeter (620) of the waist or other region of the stent-valve frame (270) as shown in FIGS. 16A-16B; the barbs (840) are comprised of barb struts (850) and barb tips (860). An upper bulb (820) can be attached to the upstream end (415) of the waist to assist with positioning the stent-valve frame (270) adjacent the native mitral valve tissues and to assist with forming a seal with the mitral annulus and the LA (230) tissues. A covering (740) can be placed and attached to portions of the stent-valve frame (270), including, for example, the upper bulb (820), the waist (300), and portions of the frustum-shaped housing (400). Since the free-edge supported replacement leaflets (280) have a linear attachment to the stent-valve frame in a circular path, the covering (740) does not need to extend on any region of the stent-valve frame (270) downstream (330) of the replacement leaflet linear attachment (630) which attaches the replacement leaflet base (550) to the stent-valve frame (270). The covering (740) ensures that blood is unable to traverse from the LV (240) to the LA without passing directly across the free edge supported replacement leaflets (280) from the LV (240) to the LA (230) in an upstream direction (865) with the leaflets in a closed configuration (608). The covering (740) also assists in reducing leakage around the outside (920) of the stent-valve frame between the stent-valve frame (270) and the native valve annulus (130) or other native valve tissues of the heart. The barbs (840) can be balloon expandable (BE) barbs (840) that are in an inactive configuration located toward the inside (870) of the stent-valve frame during delivery of the stent-valve (275) in a small diameter configuration (1120) contained within a delivery sheath (1130) as shown in FIG. 16E and during expansion of the stent-valve frame (270) to a larger diameter configuration (1140) that is in contact along its perimeter with the native tissues of the heart valve as shown in FIG. 16A. The waist contains a backing element (880) or backing member (880) such as a backing fiber (890) that is attached to the stent-valve frame and forms a fixed member against which an outward force (900) can be applied by an expanding torus balloon (910) to push the barbs (840) outwards thereby activating the barbs (840) to place the barb tips (860) into a location outside (920) of the stent-valve frame (270) as shown in FIG. 16B; the activated barbs (840) are then able to extend into native mitral valve tissues and prevent the stent-valve frame from migration to a position either upstream (865) or downstream (330). A torus balloon is located on the outside (920) of the backing element and on the inside (870) of a barb strut (850). After the stent-valve has been delivered such that the waist frame (270) has been expanded to an expanded configuration (1140) located adjacent to the annulus (130), the torus balloon is inflated to cause the barb struts (850) to extend outwards and drive the barb tips (860) to the outside (920) of the stent-valve frame (270) and into the annulus (130) as shown in FIG. 16B. The torus balloon can be implanted along with the stent-valve of the present invention; the saline, saline-based, or blood compatible inflation medium used to inflate the balloon can be allowed to leak out of the balloon inflation port over time. Further detailed description of this and other embodiments and methods of use for the torus balloon are described in earlier embodiment of the present patent application and in patent applications that are referenced herein and incorporated fully into the present patent application by reference.

Figure 16C:
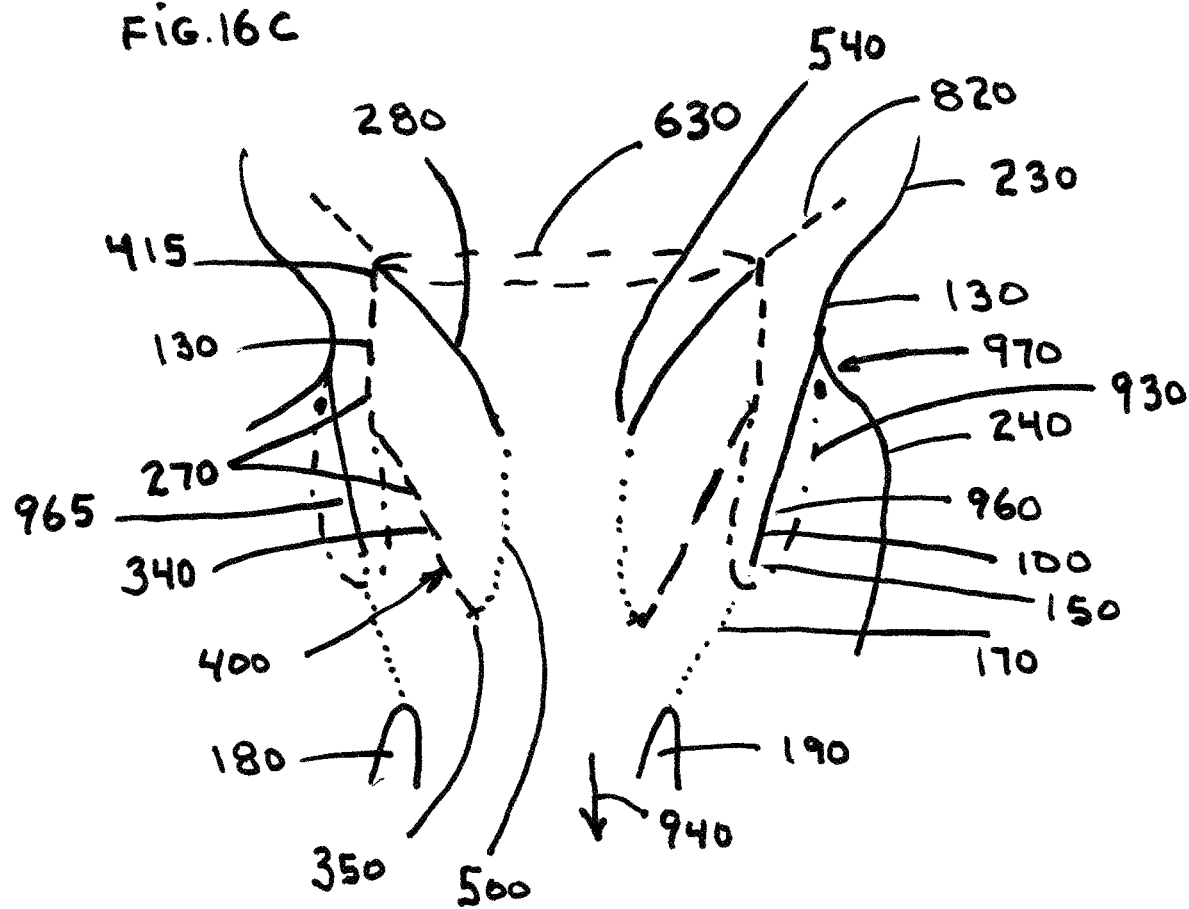
FIG. 16C is a plan side view of a single component stent-valve having an attachment antimigration mechanism that has holding arms that extends around the native mitral valve leaflets; the stent-valve frame has the base of the replacement leaflet attached to the stent-valve frame in a linear configuration and the leaflet free edges are attached to supports via cords.
Figure 16E:
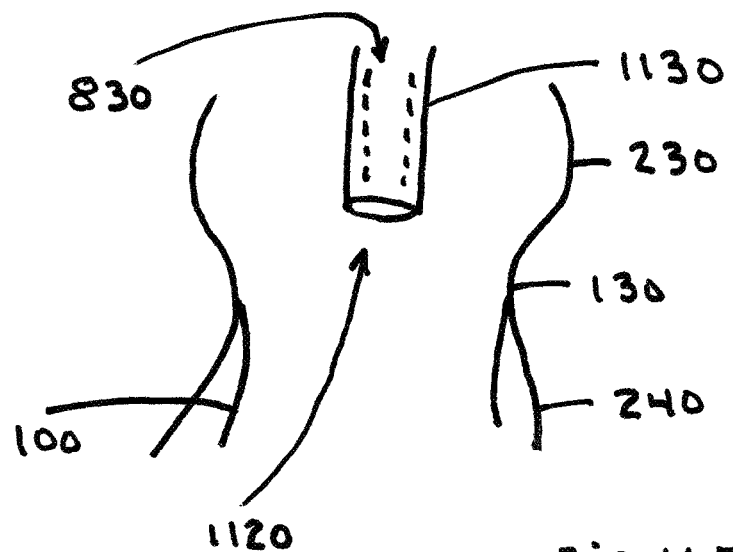
FIG. 16E is a plan view of a stent-valve frame in a small diameter configuration within a sheath.

Another method for attaching the stent-valve frame (270) of a single member stent-valve (830) containing free-edge supported leaflets of the present invention to the native heart tissue is shown in FIG. 16C. In this embodiment a plurality of holding arms (930) are attached to the stent-valve frame (270) and extend distally (940) on the luminal side (950) of the native mitral valve leaflet (100), extend around the free-edges (150) of the native mitral valve leaflets and through the cordae tendineae (170), and extend on the LV wall side (960) of the native leaflets (100) to a junction (970) of the native leaflets (100) with the mitral annulus (130) on the back side (965) of the native leaflets (100). The holding arms (930) extend to the junction of the native leaflets (110) with the mitral annulus (130) to prevent migration of the stent-valve frame (270) from the LV (240) to the LA (230) and reduce other potential movement of the stent-valve. The stent-valve frame (270) can have supports (340) attached to the waist (300) or to the frustum (400); the supports (340) having a distal end (490) that contains the fastening sites (350) to which one end of each of the cords (500) can be attached; the other end of each of the cords (500) will therein further attach to the replacement leaflet free edges (540) of the free-edge supported leaflets (280) of the present invention. The replacement leaflet base (550) is attached via a liner attachment (630) to the stent-valve frame (270). As shown in this embodiment the linear attachment (630) of the replacement leaflets (280) to the stent-valve frame (270) occurs at the junction of the waist inlet (415) to the upper bulb (820); this location for the linear attachment (630) allows the replacement leaflets (280) to have a longer leaflet length (i.e., longer than a linear attachment (630) to the frame located further distally (940)) without interfering with native mitral valve structures including the cordae tendineae and the native mitral valve leaflets. Other embodiments of the present invention can also have the linear attachment (630) located upstream on the stent-valve frame near the upper bulb in a manner similar to that shown for this embodiment.

Figure 16D:
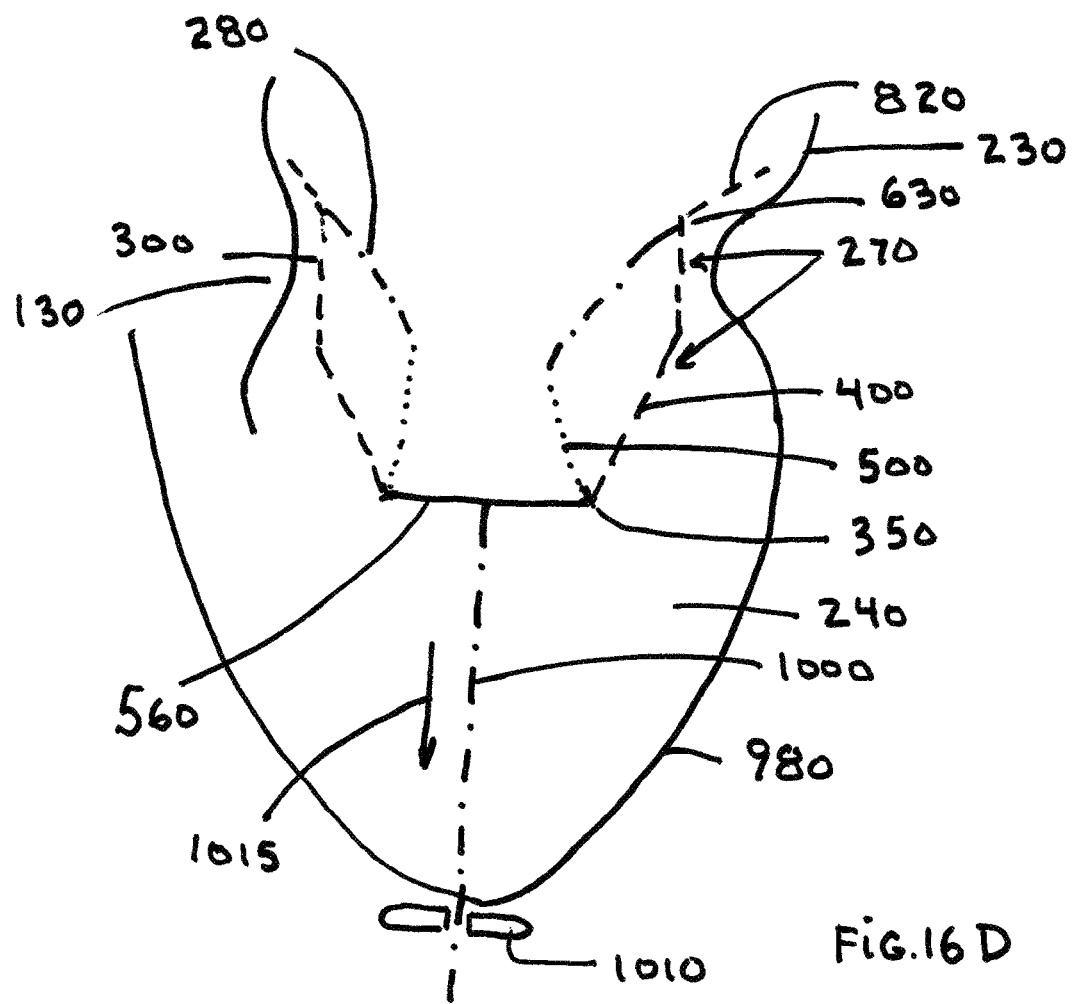
FIG. 16D is a plan side view of a single component stent-valve having an attachment antimigration mechanism that has a tether attached to the stent-valve frame, the tether extends through the myocardial tissue near the apex and attaches to a button on the outside of the heart; the stent-valve frame has the base of the replacement leaflet attached to the stent-valve frame in a linear configuration and the leaflet free edges are attached to supports via cords.

In another embodiment for a single member stent-valve (830), the stent-valve frame (270) of the present invention can be attached to the myocardial wall (980) near the LV apex (990) via a tether (1000) to hold the stent-valve frame (270) from migration from the LV (240) to the LA (230) as shown in FIG. 16D. Such a tether can be attached to a lateral support member (560) that joins between two fastening sites (350), for example. The tether extends through the myocardium and is attached via a button (1010) that slides and locks along the tether to provide the tether with adjustable tension (1015) from the stent-valve frame (270) to the myocardium of the heart (980).

The stent-valve frame (270) for the free-edge supported leaflets (280) of the present invention can also be used as a valve member (1020) or second component (1020) of a dual member stent-valve (1030) as shown in FIGS. 17A and 17B. As shown in FIG. 17A a first component (1040) or support member (1040) can be placed across the mitral valve annulus (130) and attached to the mitral annulus or other native mitral valve tissues via barbs (840) that are located along a perimeter (320) of the stent-valve frame (270) of the first component (1040) or support member (1040) (which does not contain the replacement leaflets). The first component (1040) or support member (1040) is delivered in an unexpanded configuration and is expanded outwards into contact with the mitral annulus (130) prior to activation of the barbs (840). Once the support member is located adjacent the mitral annulus, the torus balloon (910) is inflated to activate the barbs (840) to the outside (920) of the stent-valve frame (270) of the support member (1040) and into the native tissues of the mitral valve. The stent-valve frame (270) of the present invention is then placed as a valve member (1020) or second component (1020) into the open central lumen (1050) of the first component (1040) and allowed to expand into contact with the first component (1040). The second component (1020) can have a waist having a concave second component region (1060) or other geometrical shape that locks or fits geometrically with a concave first component region (1070) to prevent migration of the stent-valve frame (270) of the second component (1020) from migrating relative to the first component (1040). The stent-valve frame (270) of the second component (1020) contains the supports (340) and fastening sites (350) that are attached to cords (500) which in turn are attached at their opposite end to the replacement leaflet free edges (540) of the free-edge supported replacement leaflets (280) to prevent the replacement leaflets (280) from everting. The replacement leaflets (280) are also attached along the leaflet base (550) to the stent-valve frame (270) following a linear attachment (630) along the perimeter (320) of the stent-valve frame (270).

Another embodiment for a dual member stent-valve (1030) that uses the stent-valve frame and free-edge supported leaflets as a valve member (1020) or second component (1020) is shown in FIG. 17B. In this embodiment the first component (1040) or support member (1040) is a stent frame that does not contain the replacement leaflets (280); the first component stent frame (1045) is delivered to a location adjacent to the mitral valve tissues. A plurality of holding arms (930) are attached to the first component stent frame (1045); the holding arms extend distally (940) on the luminal side (950) of the native leaflets, around the free-edges (150) of the native leaflets (100), and proximally on the LV wall side (960) of the native leaflets (100) to a junction (970) of the native leaflets (100) with the annulus (130) or myocardial LV (240) wall. The plurality of holding arms (930) prevents migration of the first component (1040). The first component (1040) serves as a support member that allows a second component (1020) to be delivered within its open central lumen (1050) and provide a means for attachment of the second component (1020) to the first component (1040). Other embodiments for the BE barb are described in more detail in other patent applications that are referenced and are fully incorporated herein by reference.

The first component (1040) can have a geometric feature such as a concave first component region (1070) that extends along the waist or other portion of the stent-valve frame (270) of the first component (1040). The first component (1040) also resists further diametric expansion thereby providing an outer member or outer diameter limiting element (1075) (i.e., a flexible but non-stretchable fiber that extends around the perimeter of the first component frame (1045) that provides a maximum expansion diameter for the first component frame (1045)) into which a second component (1020) can be expanded under a large outward force (900) that will resist migration of the second component (1020) relative to the first component (1040) due to friction and geometrical locking between the first component (1040) and second component (1020). The second component (1020) or valve member (1020) can have the stent-valve frame (270) and free-edge supported replacement leaflets (280) of the present invention. The stent-valve frame (270) contains supports (340) that have fastening sites (350) located at the distal end (490); the fastening sites (350) attach to cords (500) that are then attached to free edges (540) of the free-edge supported replacement leaflets (280). The second component is then expanded within the open central lumen (1050) of the first component (1040). The second component (1020) can have a waist (300) of the second component stent-valve frame (270) that has a geometrical feature such as a concave second component region (1060) that will lock into the geometrical feature of the first component (1040) to prevent migration of the second component (1020). The stent-valve frame (270) can be a BE or SE stent-valve frame structure; it can be expanded outwards to generate a friction between the second component (1020) and the first component (1040) to prevent migration of the second component (1020).

Figure 18A:
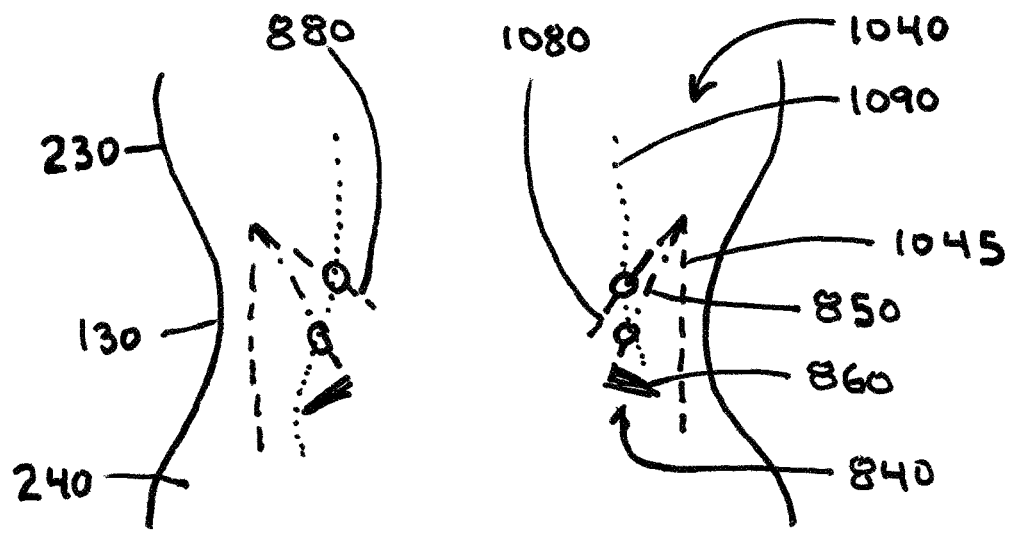
FIG. 18A is a plan view of a first component of a dual component stent-valve; the first component has self-expanding barbs are held in an inactive configuration via control fibers as the first component frame is in an expanded configuration.
Figure 18B:
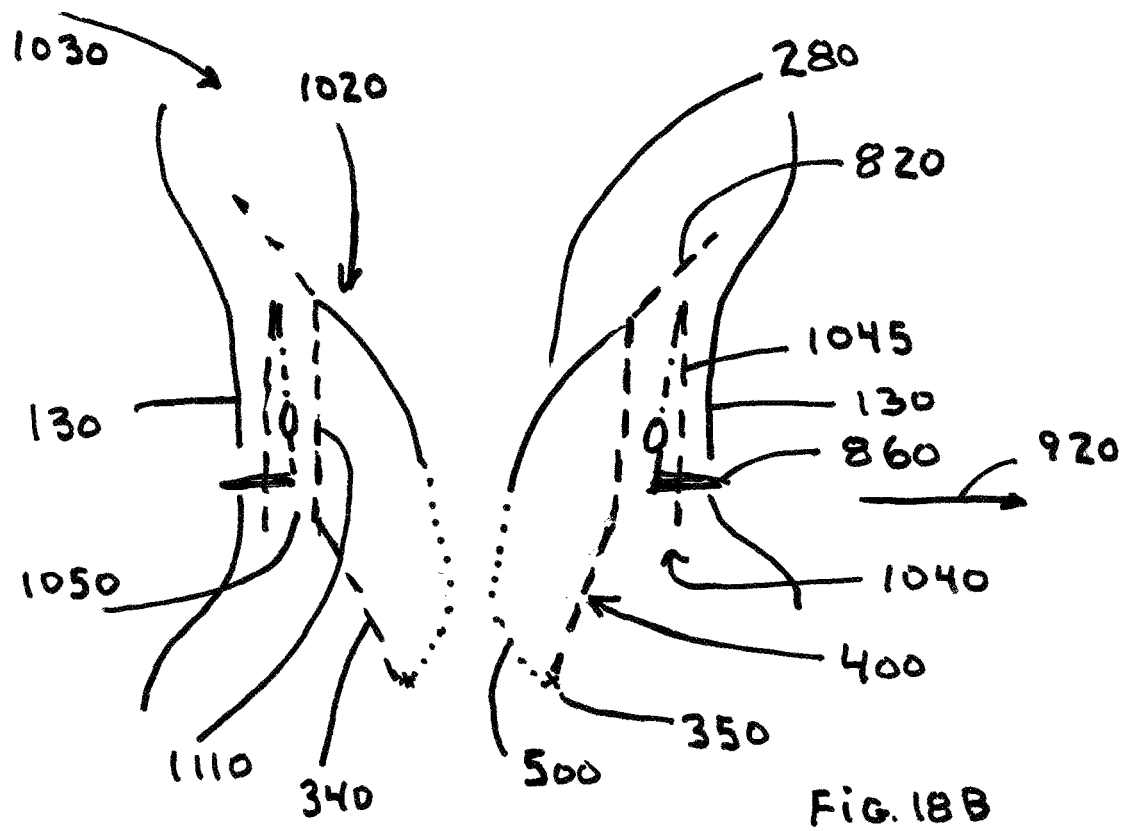
FIG. 18B is a plan view of a dual component stent-valve of FIG. 18A having a first component that is attached to the mitral valve annulus via self-expanding barbs that are activated via release of the control fibers after the first component is in an expanded configuration; a second component is placed in the open central lumen of the first component; the second component has free-edge supported replacement leaflets; the second component locks with the first component to prevent migration of the second component.

The barbs (840) that are located along the perimeter of the first component (1040) of a dual member stent-valve (1030) can alternately be SE barbs (840) that have a normal equilibrium configuration with the barbs (840) extending outwards. The first component frame (1045) has a backing elements (880) such as a plurality of stent arms (1080) attached to the first component frame (1045) and extending to the inside of the first component frame (1045) adjacent to the barbs (840) of the first component frame (1045) as shown in FIGS. 18A and 18B. During delivery to the site of the mitral valve the first component frame (1045) is contained within an external sheath and the barbs (840) are held in a retracted configuration by a control fiber (1090) that interfaces with the backing element (880) to hold the barb strut (850) inwards in an inactive configuration as shown in FIG. 18A. After the first component frame (1045) has been located adjacent the mitral annulus (130), the control fiber (1090) is released by providing tension and thereby releasing the barb strut to move outwards and causing the barb tip (860) to be located outside (920) of the first component frame (1045) and into the tissue of the annulus (130) as shown in FIG. 18B. This activation of the barb tip (860) prevents the first component frame (1045) from migrating upstream (865) or downstream (330). Following activation of the barbs (840) the second component (1020) containing the free-edge supported replacement leaflets (280) of the present invention is placed into the open central lumen (1050) of the first component (1040) as shown in FIG. 18B. The second component (1020) is located such that the second component waist (1110) is located adjacent the first component frame (1045). Such location of the second component (1020) can be attained by the presence of and upper bulb (820) that is located in the LA (230) and upstream (865) of the first component frame (1045). Also, concave geometry can be located in the first component frame (1045) and in the second component waist (1110) as described in other embodiments; such concave shapes or other geometrical shapes will self-locate the second component (1020) relative to the first component (1040) and lock the two components together such that the second component (1020) cannot migrate toward the LA (230) or the LV (240). The second component of this embodiment can have the same structure for the stent-valve frame (270) and replacement leaflets (280) as described in earlier embodiments as shown in FIG. 18B. Other embodiments for the SE barb are described in more detail in other patent applications that are referenced and are fully incorporated herein by reference.

It is further understood that the present invention for free-edge supported leaflets for a TMVR device can utilize other means for attaching the frame of the stent-valve to the native mitral tissue apparatus to prevent migration of the stent-valve; such attachment means can involve attachment to the LA (230), the mitral annulus, the mitral leaflets, the cordae tendineae, the papillary muscles, the junction of the mitral leaflets with the myocardial wall, and the myocardial wall tissue including the myocardial apex. Such approaches include clips and hooks that grab or clip the free-edges of the mitral valve, cords (500) that attach the stent-valve with the myocardial tissue near the apex, rings that surround the mitral valve leaflets adjacent the lateral myocardial wall and within the LVOT, and attaching directly to the mitral leaflet surface. The free-edge supported mitral valve leaflets provide a lower profile for the leaflets due to the direct attachment of cords (500) to the free edge (540) of the leaflets; this method for leaflet attachment differs from that found with semi-lunar valve attachment found with aortic valve, for example. The stresses found within the valve leaflet needed to support the aortic valve from eversion are greater than those found in the mitral valve even though the mitral valve has a greater surface area and the pressure found within the LV (240) are much larger than those found within the aorta. Therefore, the leaflets that are free-edge supported can be formed with a thinner profile than a semi-lunar valve that does not have any support along its free edge.

Reference numerals used in the specification and found on the drawings of the various embodiments of the present invention are intended to represent similar structures having similar functions. Also, it is understood that aspects of one or more embodiments can be combined with other aspect from another embodiment to form an embodiment that is also included in the present invention.

The free-edge supported leaflets of the present invention can be used with a variety of stent-valve frames including those embodiments presented in the present patent application and those that are incorporated in the present patent application by reference. Other frame designs are also anticipated for use with the free-edge supported leaflets of the present invention including SE and BE frame designs used for TAVR procedures or other stent-valve applications. The use of free-edge supported leaflets is not limited to those frame designs that have been described herein or have been referenced herein.

The invention claimed is:

1. A stent-valve that is deliverable via transcather delivery to a native heart valve said stent-valve directing blood flow downstream and preventing blood flow upstream in a native heart of a body, said stent-valve comprising;
- A. an expandable stent-valve frame, said stent-valve frame expanding from a smaller diameter deliverable configuration to a larger diameter configuration within the native heart valve,
- B. replacement leaflets having a leaflet base that is attached to said stent-valve frame, each of said leaflets having a leaflet free edge, said leaflet free edges forming a coaptation with another of said leaflet free edges in a closed configuration for said leaflets,
- C. said stent-valve frame further comprising fastening sites attached thereto, said fastening sites being located downstream of said replacement leaflets,
- D. each of said fastening sites having a cord attached thereto; each of said cords being attached to said fastening site by a cord first end, each of said cords further having a cord second end, said cord second end being attached to said leaflet free edge,
- E. wherein said cord prevents said leaflet free edge from everting due to blood pressure in the native heart.

2. The stent-valve of claim 1 wherein said leaflet base attachment forms a shape of a circle, an oval, or a saddle shape.

3. The stent-valve of claim 1 wherein a fastening site distance between each of said fastening sites is less than a diameter of said stent-valve frame at the location of said leaflet base attachment.

4. The stent-valve of claim 1 wherein said stent-valve frame has support members attached thereto, said support members extending downstream of said replacement leaflets to said fastening sites.

5. The stent-valve of claim 4 wherein said stent-valve frame further comprises a frustum-shaped frame, said frustum-shaped frame comprising said support members, said support members being contiguous with a wall structure of said frustum-shaped frame.

6. The stent-valve of claim 1 wherein said stent-valve frame further comprises a frustum-shaped frame, said frustum-shaped frame comprising said fastening sites.

7. The stent-valve of claim 1 wherein two fastening sites are attached to said stent-valve frame.

8. The stent-valve of claim 1 wherein three fastening sites are attached to said stent-valve frame.

9. The stent-valve of claim 1 wherein said replacement leaflets are comprised of two replacement leaflets.

10. The stent-valve of claim 9 wherein each of said two replacement leaflets is attached via said cords to a specific one of said fastening sites.

11. A stent-valve for transcatheter placement within a native heart valve to direct blood flow downstream and prevent blood flow upstream, the stent-valve comprising;
- A. an expandable stent frame, said stent frame having a small diameter configuration that is able to be delivered via standard transcatheter methods and expandable to a larger diameter configuration that is located within the native heart valve,
- B. two free-edge supported leaflets attached to said stent frame forming an attachment, said free edge supported leaflets having free edges that form a coaptation of said free-edge supported leaflets in a closed configuration,
- C. a first support member and a second support member contiguous with or attached to said stent frame and extending downstream of said free edges; said first support member having a first fastening site at a distal end of said first support member and said second support member having a second fastening site at a distal end of said second support member,
- D. said first fastening site being attached to a first end of a first cord, said second fastening site being attached to a first end of a second cord,
- E. a second end of said first cord being attached to said free edge of a first leaflet of said free-edge supported leaflets, a second end of said second cord being attached to said free edge of a second leaflet of said free-edge supported leaflets,
- F. wherein said first cord and said second cord prevent said first leaflet and said second leaflet from everting and thereby preventing passage of blood flow upstream.

12. The stent-valve of claim 11 wherein said first fastening site is separated from said second fastening site by a fastening site distance that is smaller than a diameter for said stent frame in said larger diameter configuration.

13. A stent-valve that is deliverable to a native heart valve, said stent-valve directing blood flow downstream and preventing blood flow upstream in a native heart of the body, said stent-valve comprising;
- A. an expandable stent-valve frame, said stent-valve frame expanding from a smaller diameter deliverable configuration to a larger diameter configuration within the native heart valve,
- B. replacement leaflets having a leaflet base that is attached to said stent-valve frame, each of said leaflets having a leaflet free edge, said leaflet free edge forming a coaptation with another of said leaflet free edge in a closed configuration for said leaflets,
- C. said stent-valve frame comprising fastening sites attached thereto, said fastening sites being located downstream of said leaflet free edges,
- D. each of said fastening sites having a separate cord attached thereto; each of said cords being attached to said fastening site by a cord first end, each of said cords further having a cord second end, said cord second end being attached to said leaflet free edge,
- E. wherein said separate cords preventing said leaflet free edges from everting due to blood pressure in the native heart.

* * * * *